(12) United States Patent
Walker

(10) Patent No.: US 7,546,993 B1
(45) Date of Patent: Jun. 16, 2009

(54) FLEXIBLE CLAMPING APPARATUS FOR MEDICAL DEVICES

(75) Inventor: Clarence Walker, St. Louis, MO (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 12/055,161

(22) Filed: Mar. 25, 2008

(51) Int. Cl.
*A47B 96/06* (2006.01)

(52) U.S. Cl. .............................. 248/218.4; 248/229.12; 248/229.22

(58) Field of Classification Search .............. 248/218.4, 248/219.4, 160, 231.41, 229.12, 229.22, 248/228.3, 230.3, 231.71, 104, 230.6, 229.15, 248/229.1; 403/286, 293, 373, 374.5
See application file for complete search history.

(56) References Cited

U.S. PATENT DOCUMENTS

| | | | |
|---|---|---|---|
| 184,957 A | 12/1876 | Doeg | |
| 252,969 A | 1/1882 | Porter | |
| 291,248 A | 1/1884 | West | |
| 989,893 A | 4/1911 | Brick | |
| 1,059,217 A | 4/1913 | Rudy | |
| 1,066,357 A | 7/1913 | Yardley | |
| 1,160,103 A | 11/1915 | Burkhart | |
| 1,403,863 A | 1/1922 | Peat | |
| 1,749,491 A | 3/1930 | Kokay | |
| 2,101,317 A | 12/1937 | Lemieux | |
| 2,116,263 A | 5/1938 | Harbaugh | |
| 2,269,790 A * | 1/1942 | Sherrill | ..................... 24/132 R |
| 2,322,107 A | 6/1943 | Balcar | |
| 2,448,402 A | 8/1948 | Thompson | |
| 2,638,301 A | 5/1953 | Smith | |
| 2,756,789 A | 7/1956 | Kraus et al. | |
| 2,867,003 A | 1/1959 | Stiles | |
| 2,945,946 A | 7/1960 | Moffatt | |
| 3,268,853 A | 8/1966 | Noker et al. | |
| 3,442,478 A | 5/1969 | Parapetti | |
| 3,803,012 A | 4/1974 | Kurr | |
| 3,883,128 A | 5/1975 | Breese | |
| 4,120,130 A * | 10/1978 | Puschkarski | ............... 52/282.5 |
| 4,164,344 A | 8/1979 | Deragne | |
| 4,262,872 A | 4/1981 | Kodet | |
| 4,365,792 A | 12/1982 | Johns | |
| 4,432,538 A | 2/1984 | Sequin | |
| 4,443,128 A | 4/1984 | Yamamoto et al. | |
| 4,487,523 A | 12/1984 | Monroe | |

(Continued)

FOREIGN PATENT DOCUMENTS

EP       0167345 A1    1/1986

*Primary Examiner*—Ramon O Ramirez
(74) *Attorney, Agent, or Firm*—Edward S. Jarmolowicz, Esq.

(57) ABSTRACT

A clamping apparatus of the present invention is used in a medical environment to rotationally and releasably secure a device to a support member. The clamping apparatus includes a device clamp having first and second clamp elements and a connector interconnecting the clamp elements. The clamp elements define a first receptacle for receiving a support and a second receptacle for receiving a mounting structure. At least one clamping element defines a device catch in the second receptacle. The connector is selectively moveable between a first position in which relative rotation between the flexible shaft, device clamp and device is resisted, and a second position in which the device is permitted to rotate without releasing connection to the support. A method of supporting a medical device on a support to permit selective rotation of the medical device relative to a flexible shaft without loss of interconnection is also disclosed.

25 Claims, 20 Drawing Sheets

U.S. PATENT DOCUMENTS

| | | |
|---|---|---|
| 4,500,077 A | 2/1985 | Coxon |
| 4,504,046 A | 3/1985 | Yonezawa et al. |
| 4,547,092 A | 10/1985 | Vetter et al. |
| 4,560,152 A | 12/1985 | Miller |
| 4,576,501 A | 3/1986 | McConnell |
| 4,676,687 A | 6/1987 | Koffler |
| 4,695,025 A | 9/1987 | Vaughan |
| 4,697,800 A | 10/1987 | Stahl et al. |
| 4,699,344 A | 10/1987 | Vaughan |
| 4,702,448 A | 10/1987 | LoJacono et al. |
| 4,706,368 A | 11/1987 | Crissman, III et al. |
| 4,742,981 A | 5/1988 | Converse |
| 4,796,846 A | 1/1989 | Meier et al. |
| 4,832,294 A | 5/1989 | Eidem |
| 4,832,299 A | 5/1989 | Gorton et al. |
| 4,842,174 A | 6/1989 | Sheppard et al. |
| 4,850,099 A | 7/1989 | Scollard |
| 4,852,841 A | 8/1989 | Sebring |
| 4,865,484 A | 9/1989 | McConnell |
| 4,881,843 A | 11/1989 | Randleman |
| 4,885,667 A | 12/1989 | Selden |
| 4,957,021 A | 9/1990 | Helton |
| 4,958,873 A | 9/1990 | Akagawa |
| 4,969,768 A | 11/1990 | Young |
| 4,982,988 A | 1/1991 | Murphy |
| 5,025,780 A | 6/1991 | Farley |
| 5,108,213 A | 4/1992 | Shields |
| 5,118,127 A | 6/1992 | Partington |
| 5,139,359 A | 8/1992 | Rakar et al. |
| 5,161,787 A | 11/1992 | Hobday |
| 5,163,752 A | 11/1992 | Copeland et al. |
| 5,174,533 A | 12/1992 | Pryor et al. |
| 5,197,360 A | 3/1993 | Wooster, Jr. |
| 5,226,638 A | 7/1993 | Ausilio |
| 5,236,213 A | 8/1993 | Trickett |
| 5,242,240 A | 9/1993 | Gorham |
| 5,246,217 A | 9/1993 | Brot |
| 5,312,094 A | 5/1994 | Zera |
| 5,314,175 A | 5/1994 | Izumi et al. |
| 5,320,444 A | 6/1994 | Bookwalter et al. |
| 5,326,059 A | 7/1994 | Pryor et al. |
| 5,332,184 A | 7/1994 | Davis |
| 5,342,011 A | 8/1994 | Short |
| 5,346,194 A | 9/1994 | Coffin, III |
| 5,385,324 A | 1/1995 | Pryor et al. |
| 5,415,383 A | 5/1995 | Ausilio |
| 5,443,246 A | 8/1995 | Peterson |
| 5,454,551 A | 10/1995 | Hobday |
| 5,476,252 A | 12/1995 | Yonezawa |
| 5,501,435 A | 3/1996 | Monteiro |
| 5,516,088 A | 5/1996 | Coffin, III |
| 5,529,297 A | 6/1996 | Sawdon |
| 5,580,035 A | 12/1996 | Ffield et al. |
| 5,582,379 A | 12/1996 | Keselman et al. |
| 5,586,754 A | 12/1996 | Williams |
| 5,595,375 A | 1/1997 | Bennhausen |
| 5,615,968 A | 4/1997 | Verenski et al. |
| 5,657,972 A | 8/1997 | Blatt |
| 5,664,750 A | 9/1997 | Cohen |
| 5,695,177 A | 12/1997 | Mascola |
| 5,704,577 A | 1/1998 | Gordon |
| 5,727,899 A | 3/1998 | Dobrovolny |
| 5,733,061 A | 3/1998 | Child |
| 5,746,422 A | 5/1998 | Harada et al. |
| 5,807,333 A | 9/1998 | Osborne et al. |
| 5,820,116 A | 10/1998 | Haese |
| 5,826,310 A | 10/1998 | Hobday |
| 5,827,026 A | 10/1998 | Patti |
| 5,836,573 A | 11/1998 | Hayashi et al. |
| 5,868,710 A | 2/1999 | Battiato et al. |
| 5,873,386 A | 2/1999 | Arosio |
| 5,892,344 A | 4/1999 | Cooley |
| 5,899,445 A | 5/1999 | Kimble |
| 5,913,509 A | 6/1999 | Price et al. |
| 6,024,350 A | 2/2000 | Price et al. |
| 6,039,313 A | 3/2000 | Baculy |
| 6,073,285 A | 6/2000 | Ambach et al. |
| 6,073,920 A | 6/2000 | Colley |
| 6,079,703 A | 6/2000 | Chavez, Jr. |
| 6,102,383 A | 8/2000 | Tünkers |
| 6,109,602 A | 8/2000 | Schron, Jr. et al. |
| 6,139,000 A | 10/2000 | Price et al. |
| 6,241,231 B1 | 6/2001 | Schron, Jr. et al. |
| 6,326,059 B1 | 12/2001 | Lewin et al. |
| 6,338,478 B2 | 1/2002 | Baculy |
| 6,340,154 B1 | 1/2002 | Young |
| 6,382,576 B1 | 5/2002 | Heimbrock |
| 6,394,437 B1 | 5/2002 | Yonezawa |
| 6,398,175 B1 * | 6/2002 | Conner et al. ............ 248/228.3 |
| 6,402,130 B1 | 6/2002 | Price et al. |
| 6,402,131 B1 | 6/2002 | Baculy |
| 6,481,204 B1 | 11/2002 | Yuschak et al. |
| 6,520,495 B1 | 2/2003 | La Mendola |
| 6,560,798 B2 | 5/2003 | Welling et al. |
| 6,619,599 B2 | 9/2003 | Elliott et al. |
| 6,634,823 B2 | 10/2003 | Sciortino |
| 6,644,636 B1 | 11/2003 | Ryan |
| 6,690,280 B2 | 2/2004 | Citrenbaum et al. |
| 6,758,467 B2 | 7/2004 | Kitaura |
| 6,942,637 B2 | 9/2005 | Cartledge et al. |
| 6,942,647 B2 | 9/2005 | Nickels |
| 7,395,563 B2 | 7/2008 | Whitmore, III et al. |
| 2005/0006542 A1 | 1/2005 | Henning et al. |
| 2005/0053422 A1 * | 3/2005 | Porco ........................ 403/373 |
| 2005/0092877 A1 * | 5/2005 | Carnevali .................... 248/160 |
| 2005/0267449 A1 | 12/2005 | Edoga et al. |
| 2006/0278785 A1 | 12/2006 | Wiesner et al. |
| 2007/0129634 A1 | 6/2007 | Hickey et al. |
| 2007/0220671 A1 | 9/2007 | Vanderheiden et al. |

* cited by examiner

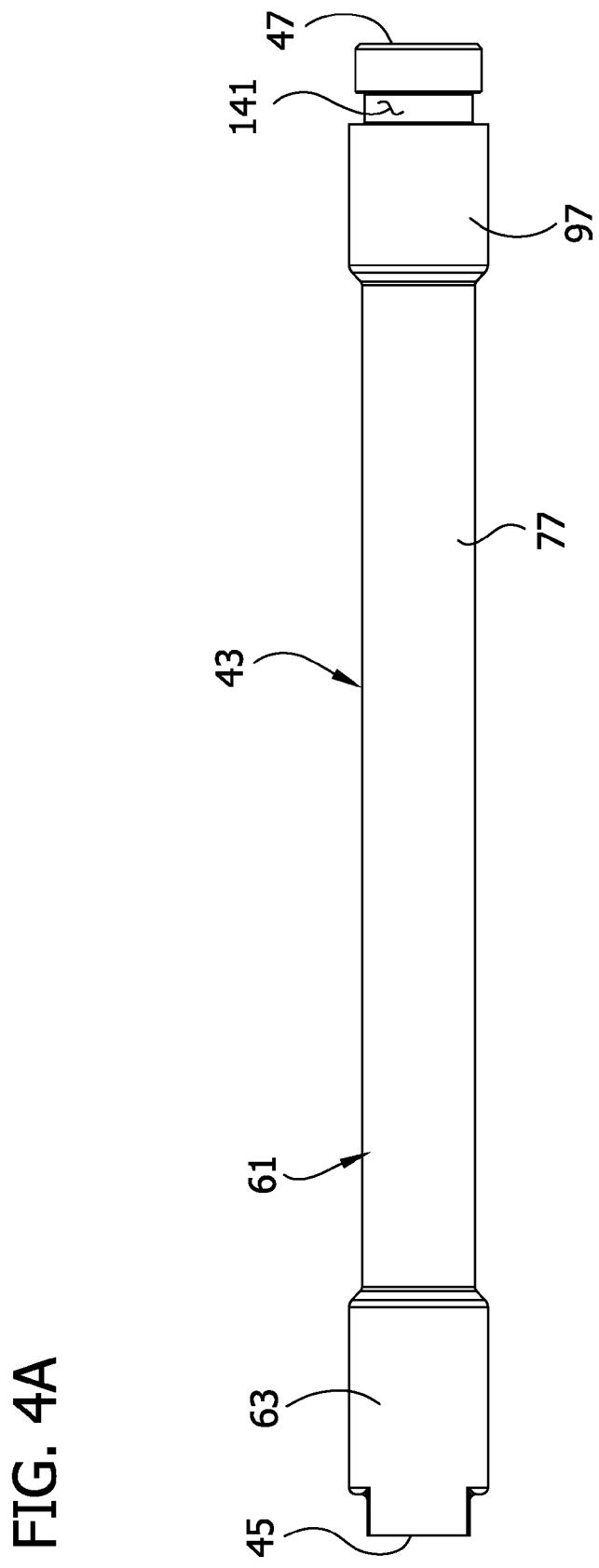

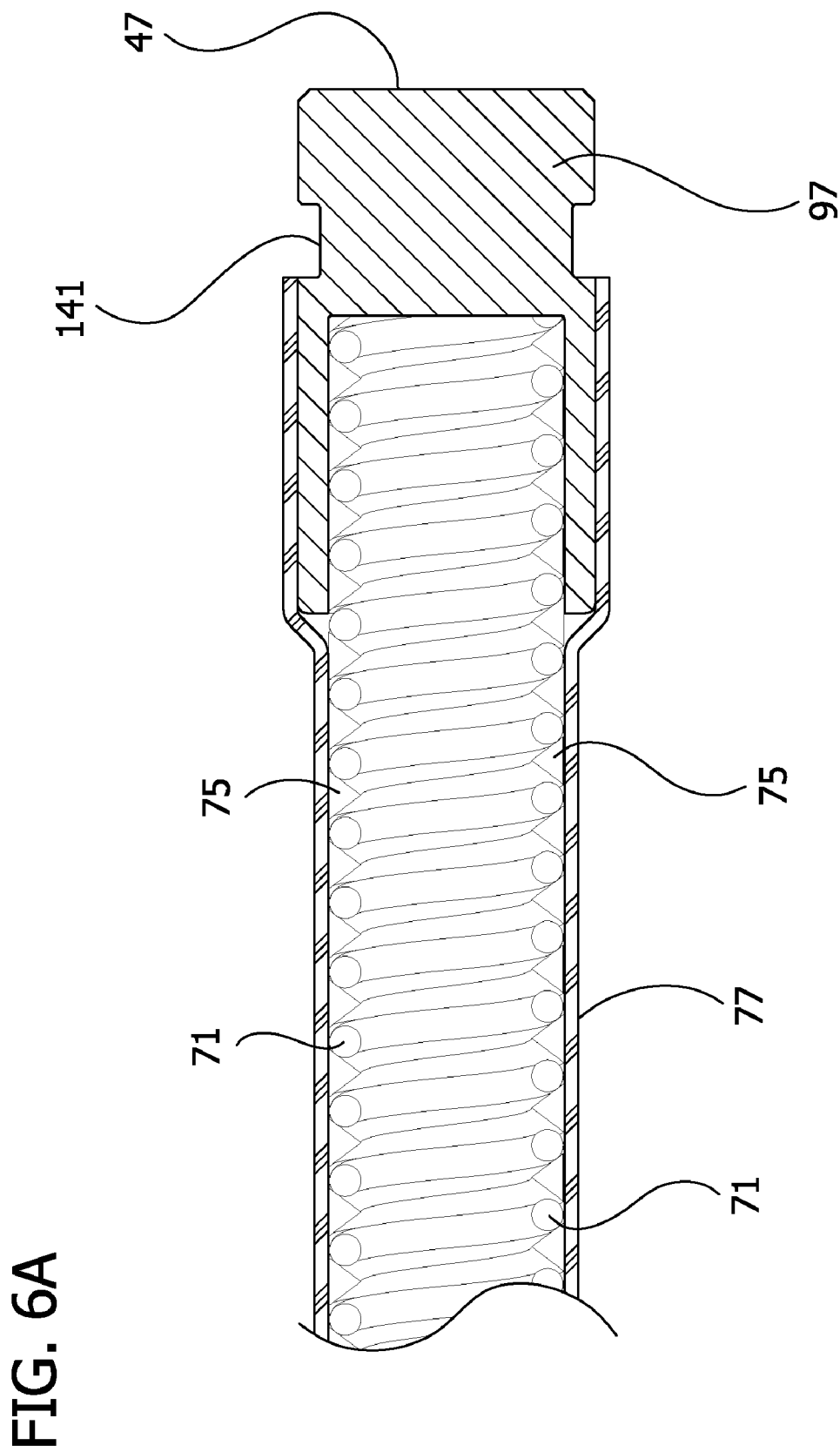

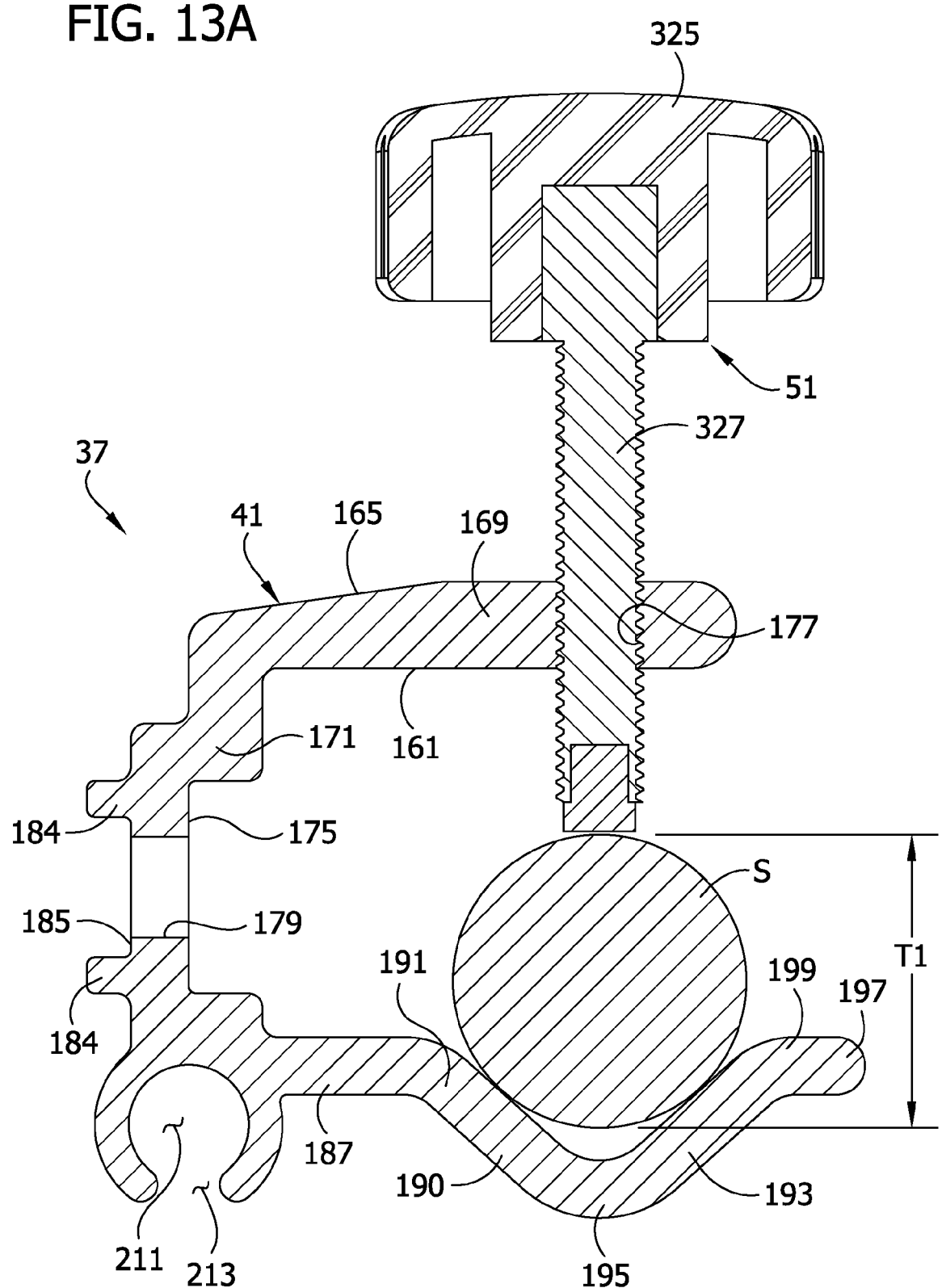

FLEXIBLE CLAMPING APPARATUS FOR MEDICAL DEVICES

FIELD OF THE INVENTION

This invention relates generally to the field of support apparatus for medical devices and more particularly to a medical device mounting apparatus having a clamping apparatus.

BACKGROUND OF THE INVENTION

Medical devices such as enteral feeding pumps are typically attached to an IV pole or other support member by a pole clamp or other attachment device that holds the pump in a fixed position relative to the support member. One existing pole clamp design permits one degree of freedom of motion of the pump relative to the pole by allowing the pump to be rotated or indexed between fixed orientations relative to the IV pole. The indexing requires a substantial portion of the fixture be located on the clamp. Another existing pole clamp design permits two or more degrees of freedom of motion such that the pump may be moved horizontally, vertically, or laterally relative to the IV pole for easier viewing and operation. An example is embodied in co-assigned application Ser. No. 11/138,200 entitled Flexible Clamping Apparatus for Medical Devices filed May 26, 2005, the disclosure of which is incorporated herein by reference.

Furthermore, such existing pole clamps are typically mounted directly on the housing of the pump so that the pump housing is in close proximity to the IV pole. As such, the pumps mounted by conventional pole clamps take up more vertical space on the IV pole that may be needed for other devices and/or medical fluid containers. These existing designs are ill-equipped for moving equipment in and out of the way at bedside as needed when providing medical care. Therefore, a need exists for a simple effective means of releasably securing a pump or similar device to a support while also allowing adjustment of the pump without releasing the pump's connection to the support.

SUMMARY OF THE INVENTION

In one aspect of the present invention, a clamping apparatus used in a medical environment to releasably secure a device to a support member generally comprises a flexible shaft having a first end for attachment to the support member and a second end for attachment to the device. A device clamp is adapted to connect the device to the flexible shaft. The device clamp comprises first and second generally opposed clamp elements and a connector interconnecting the first and second clamp elements. The first and second clamp elements define a first receptacle for receiving the second end of the flexible shaft therein and a second receptacle for receiving a mounting structure of the device therein. At least one of the first and second clamp elements defines a device catch in the second receptacle. The connector is selectively moveable between a first position in which the clamp elements are adapted to frictionally engage the second end of the flexible shaft and the mounting structure of the device to resist relative rotation between the flexible shaft, device clamp and device; and a second position in which the clamp elements are relatively farther apart than in the first position and the device catch is position to prevent withdrawal of the mounting structure of the device from the second receptacle thereby permitting the device to be rotated with respect to the flexible shaft without releasing connection to the flexible shaft.

In another aspect, a clamp for use in connecting a medical device to a support generally comprises first and second generally opposed clamp elements and a connector interconnecting the first and second clamp elements. The first and second clamp elements define a first receptacle for receiving an end of the support therein and a second receptacle for receiving a mounting structure of the medical device therein. At least one of the first and second clamp elements defines a device catch in the second receptacle. The connector is selectively movable between a first position in which the clamp elements are adapted to frictionally engage the end of the support and the mounting structure of the device to resist relative rotation between the support, clamp and medical device; and a second position in which the clamp elements are relatively farther apart than in the first position and the device catch is positioned to prevent withdrawal of the mounting structure of the medical device from the second receptacle thereby permitting the device to be rotated with respect to the support without releasing connection to the support.

In yet another aspect, a method of supporting a medical device on a flexible shaft to permit selective rotation of the medical device relative to the flexible shaft without loss of interconnection with the shaft generally comprises rotating a connector to move first and second clamp elements to an open position. Inserting a mounting structure of the medical device into a second receptacle defined by the first and second clamp elements. Then rotating the connector to move the first and second clamp elements to a fully closed position thereby clamping the mounting structure in a receptacle defined by the first and second clamp elements for resisting relative rotation of the mounting structure relative to the flexible shaft. Lastly, loosening the clamp to a position in which the mounting structure and medical device are free to rotate, while the medical device is retained from moving out of the receptacle.

Other objects and features will be in part apparent and in part pointed out hereinafter.

BRIEF DESCRIPTION OF THE DRAWINGS

FIG. 4A is a side elevation of the flexible shaft;

FIG. 6A is an enlarged detail of FIG. 6 showing a sleeve of the flexible shaft;

FIG. 13A is a cross-section taken along the plane including 13A-13A of FIG. 13;

Corresponding reference characters indicate corresponding parts throughout the drawings.

DESCRIPTION OF THE PREFERRED EMBODIMENTS

Figure 1:
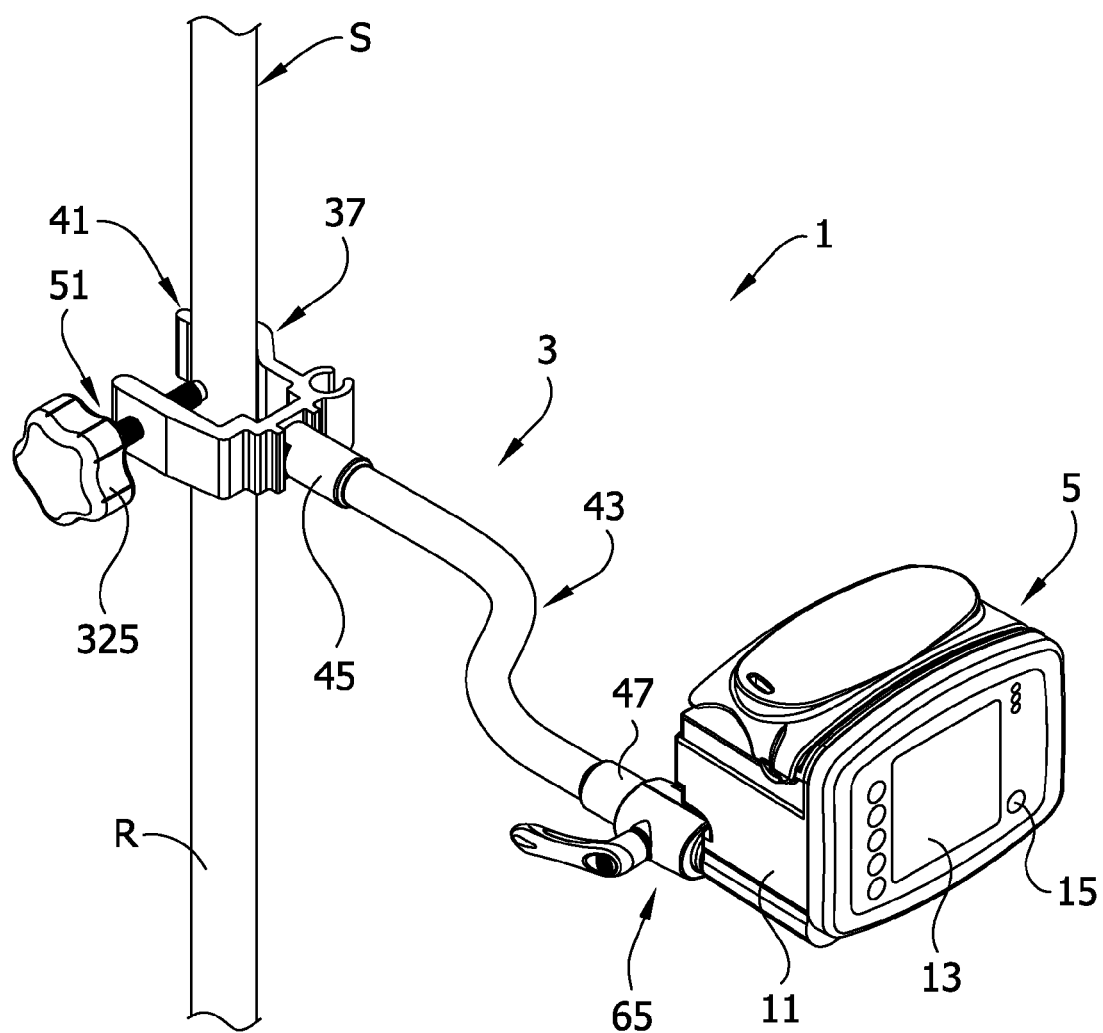
FIG. 1 is a perspective of a clamping apparatus mounting an enteral feeding pump to an IV pole.
Figure 2:
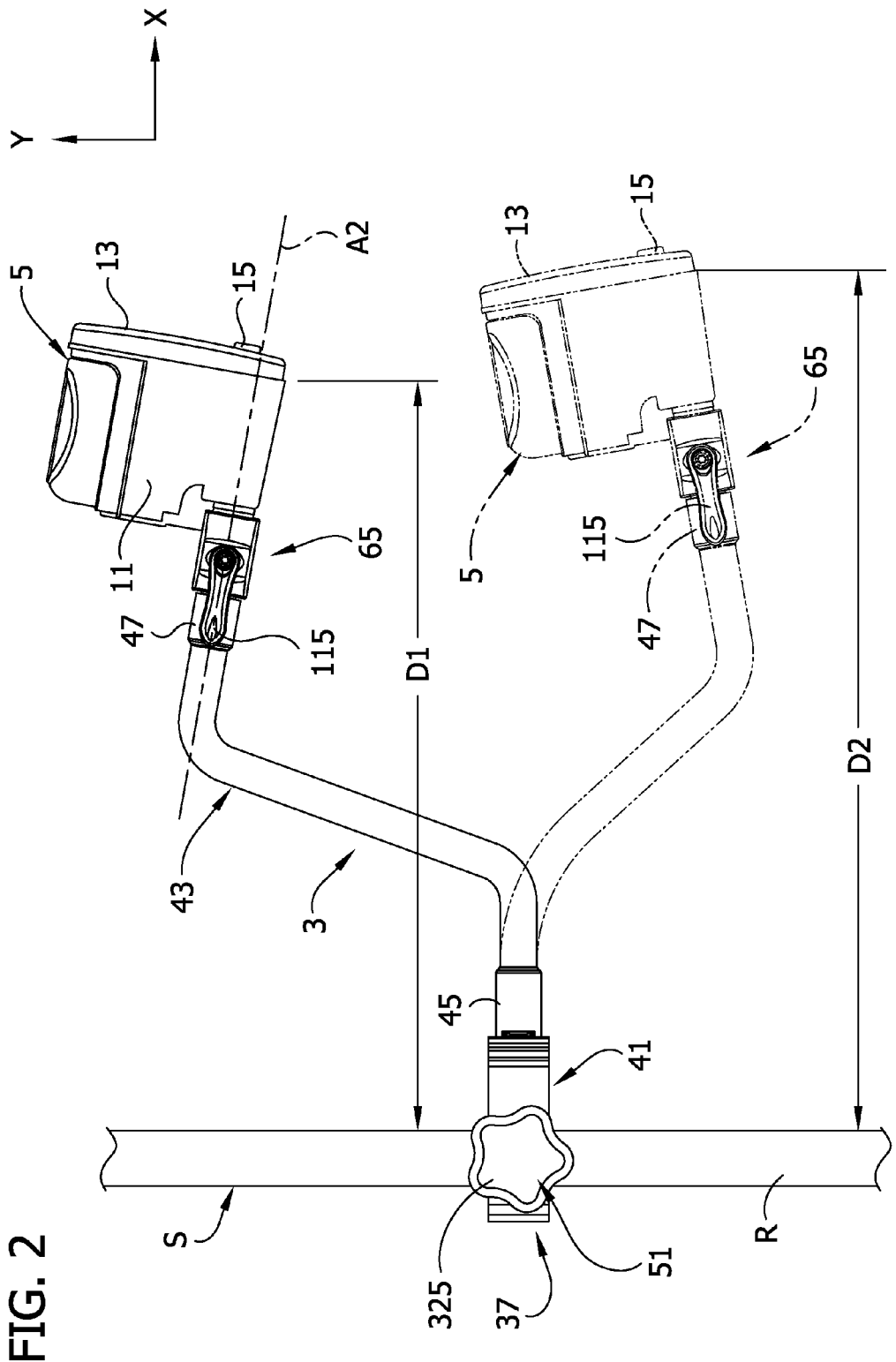
FIG. 2 is a left side elevation of FIG. 1 with adjusted position of pump shown in phantom.
Figure 3:
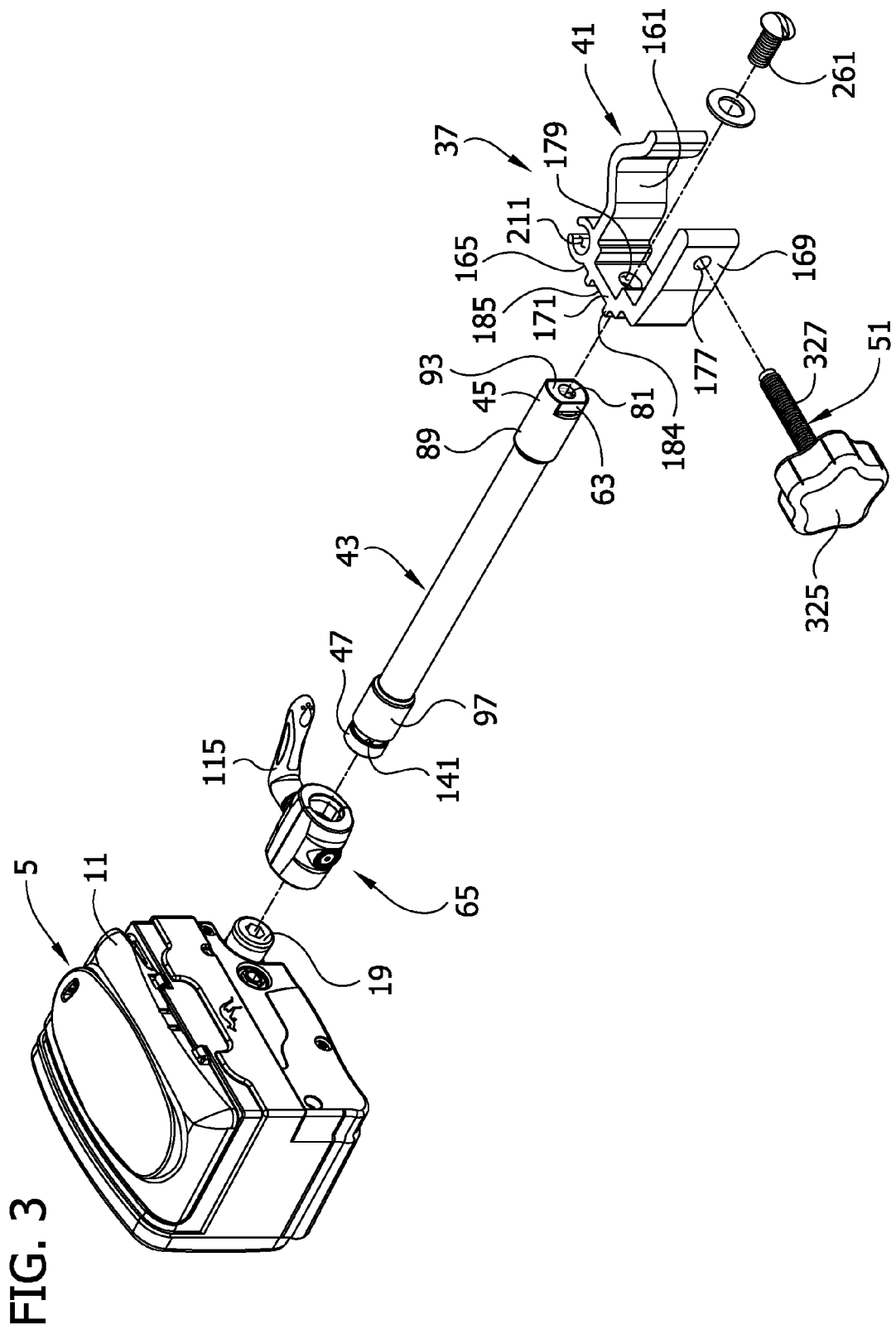
FIG. 3 is a rear perspective of the clamping apparatus and medical device with the clamping apparatus exploded.

Referring now to the drawings and in particular to FIGS. 1-3, a powered medical device assembly 1 includes a clamping apparatus 3 releasably attached to a support member S to support a medical device 5 on the support member (the reference numerals designating their subjects generally). In the embodiment of FIG. 1, the support member S is a vertical IV pole having a cylindrical rod R extending up from a stand (not shown) that is commonly used to support medical paraphernalia such as IV bags (not shown) in a hospital or other healthcare environment. As discussed further below, the clamping apparatus 3 is capable of mounting the medical device 5 on support members having other than cylindrical shapes. The clamping apparatus 3 is configured to allow full range of motion (i.e., six-degrees of freedom of motion) of the medical device 5 relative to the support member S so the medical device can be positioned for better viewing and adjustment. The clamping apparatus 3 may be more broadly described as "mounting apparatus", as it will be understood that an apparatus that mounts a medical device without clamping (e.g., including even a permanent attachment) falls within a broader scope of the present invention.

The medical device 5 may be any medical device used in diagnosing, monitoring, or treating a patient. In the illustrated embodiment, the medical device 5 is an enteral feeding pump used to regulate the delivery of nutritional fluids to a patient from a container (not shown) but it is understood that the medical device could be any other type of device that is typically mounted on a support. In the illustrated embodiment, the pump 5 has a housing 11, a display screen 13 at the front of the housing for monitoring the operational status of the pump and a control knob 15 for making adjustments to the pump. As shown in FIG. 3, the pump 5 has a mounting stem 19 (broadly, "mounting structure") attached to the back of the housing 11 for releasable attachment to the clamping apparatus 3. The mounting stem 19 is cylindrical and extends from the housing 11. It is understood that the pump 5 may be battery operated or may have a power cord (not shown) connection. The pump may be powered in any suitable manner, such as by fluid or air power. It is envisioned that the pump 5 may also be fluid (e.g., air) powered.

The clamping apparatus 3 includes a clamp, generally indicated 37, having a clamping member, generally indicated 41, for releasable attachment of the assembly 1 to the support member S and a securing rod 51 releasably attached to the clamping member for attaching the apparatus to the IV pole. The clamping apparatus 3 further includes a flexible shaft, generally indicated 43, attached to the clamping member 41 at a first end 45 and releasably attached to the medical device 5 at a second end 47 through a sleeve 97. The flexible shaft 43 is selectively configurable while connected to the pump 5 to allow the pump to have complete freedom of motion relative to the support member S. The complete freedom of motion of the pump 5 relative to the support member S includes translation of the pump in any of the three dimensions (e.g., x, y, and z-axis) relative to the support as well as rotation or the ability to change the angle of orientation of the pump relative to any of the three axes so that the pump has six degrees of freedom of motion relative to the support. Moreover, once moved the clamping apparatus 3 retains the medical device 5 in its new selected position.

Figure 4:
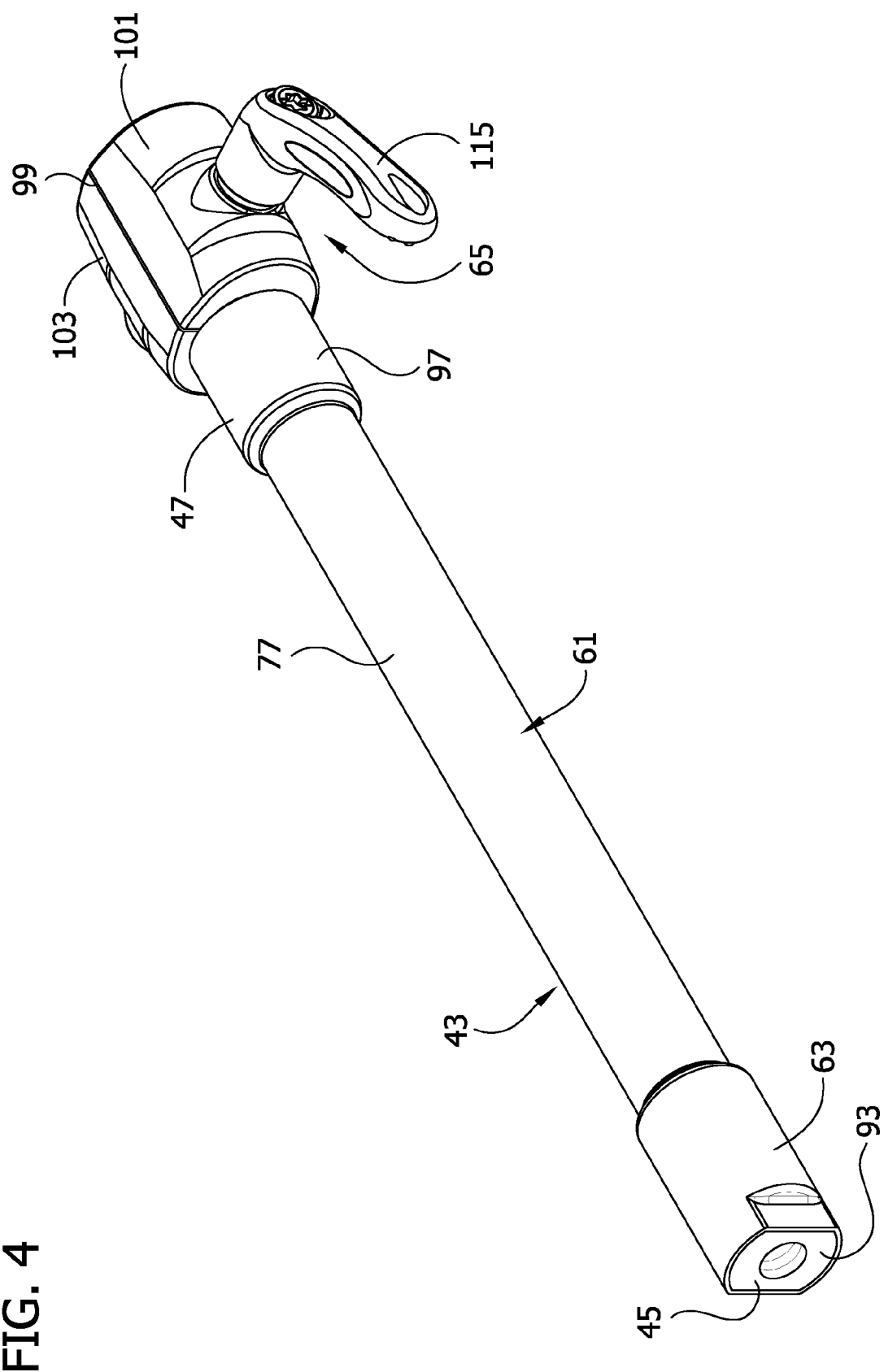
FIG. 4 is a perspective of a flexible shaft and device clamp of the clamping apparatus.
Figure 5:
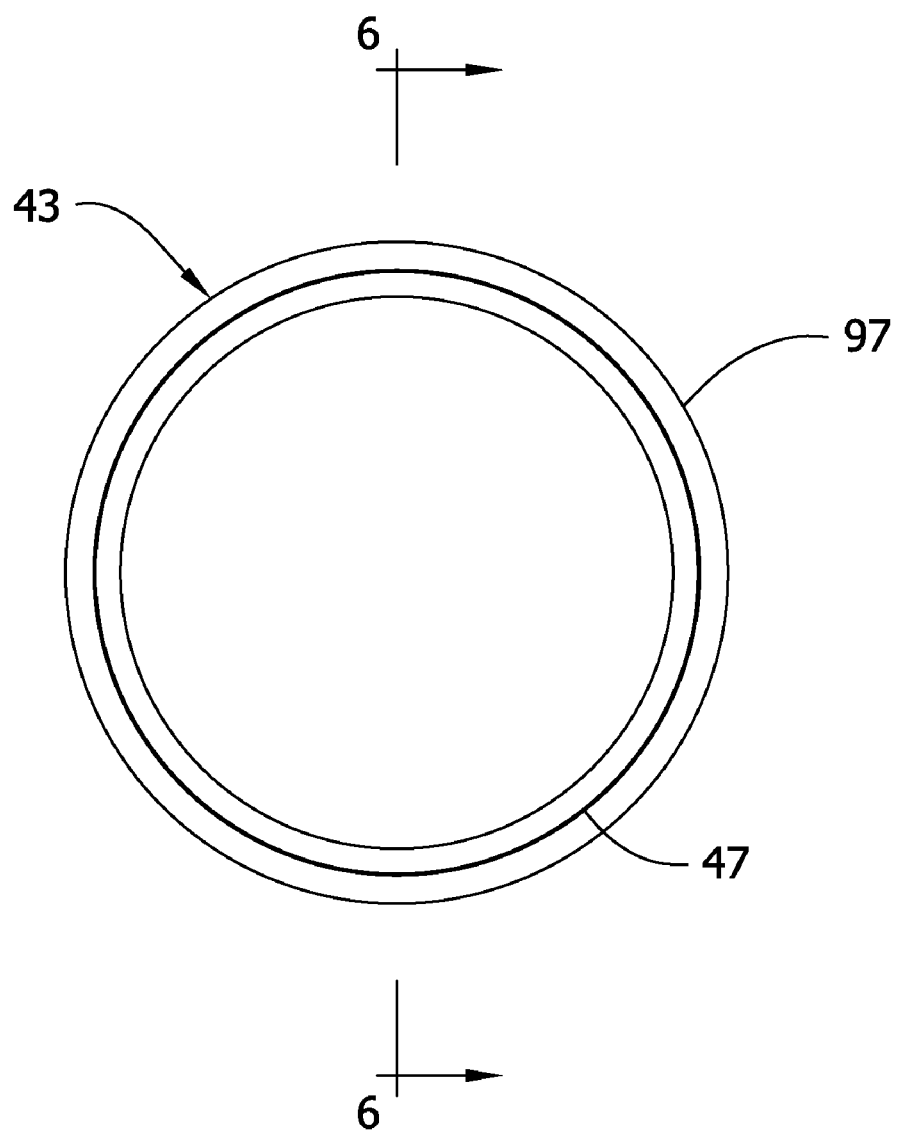
FIG. 5 is an end view of the flexible shaft.
Figure 6:
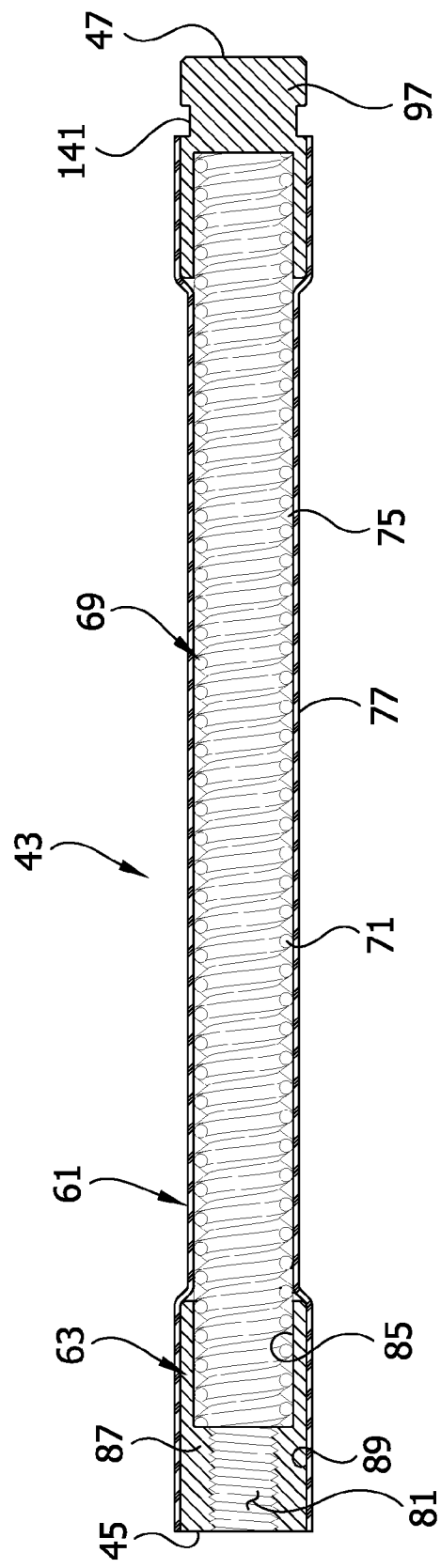
FIG. 6 is a section of the flexible shaft taken in the plane including line 6-6 of FIG. 5.

As shown in FIGS. 4, 4A and 6, the flexible shaft 43 has a generally tubular body, generally indicated 61, with an internally threaded bushing 63 mounted on the body at the first end 45 of the shaft and a device clamp, generally indicated 65, mounted on the body at the second end 47 of the shaft. As shown in FIG. 6, the tubular body 61 includes a coil spring, generally indicated 69, having a plurality of coils 71 extending from the first end 45 to the second end 47 of the shaft 43. A stiffener 75 is disposed between the coils 71 to provide stiffness to the flexible shaft 43 and allow the shaft to be set in a stationary position when bent. In the illustrated embodiment, the stiffener 75 comprises a wire having a triangular cross-section but it is understood that the stiffener may have other shapes. The stiffener 75 is pliable to allow the spring 69 to bend and twist in any direction but provides sufficient resistance to prevent the spring from returning to its original position and shape. A sheath 77 covers the spring 69 and the stiffener 75 to provide a thin outer layer for the flexible shaft 43. The sheath 77 may be made from plastic, rubber, vinyl, or any other flexible material. It is understood that the flexible shaft 43 may include a tube stiffener made out of a rigid material (e.g. copper, plastic, etc.) or an internal stiffener received through the coil spring without departing from the scope of the invention.

Referring now specifically to FIG. 6, the threaded bushing 63 mounted on the first end 45 of the flexible shaft 43 has a threaded axial bore 81 at its outer end that opens to an axial cavity 85 at its inner end that receives the spring 69 and the stiffener 75 of the flexible shaft 43. The threaded bushing 63 includes a collar 87 having an external surface 89 of the flexible shaft 43 covered by the sheath 77 that may be grasped for connecting the flexible shaft 43 to the clamping member 41. As shown in FIG. 3, the outer axial surface of the bushing has a rectangular protrusion 93 slightly greater in width than the diameter of the threaded bore 81. At the second end 47 of the flexible shaft 43 the sleeve 97 has a first annular recess 141 which will be explained later in greater detail.

Figure 7:
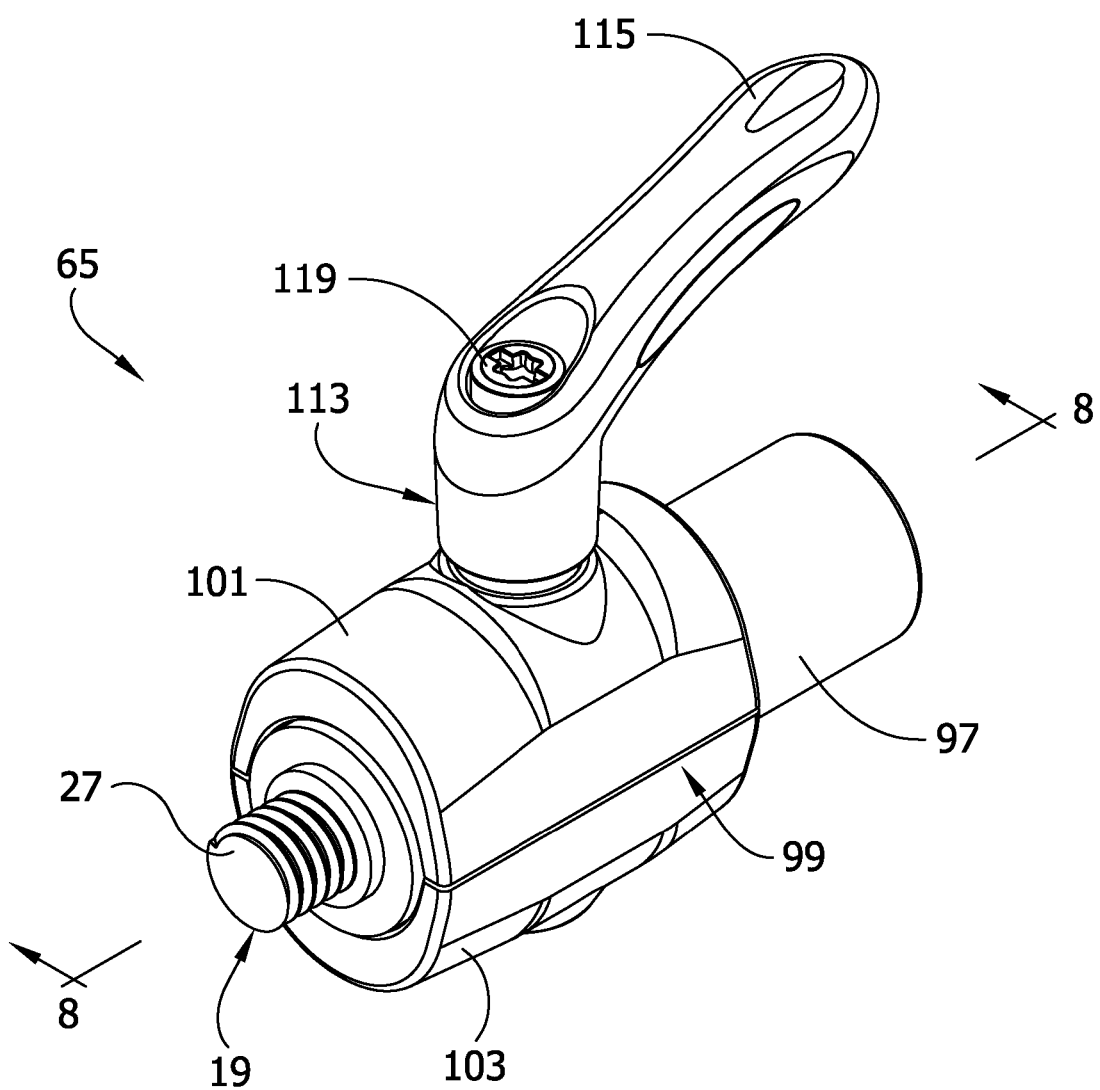
FIG. 7 is an enlarged perspective of the device clamp showing additionally a stem and a sleeve of the clamping apparatus received in the device clamp.
Figure 8:
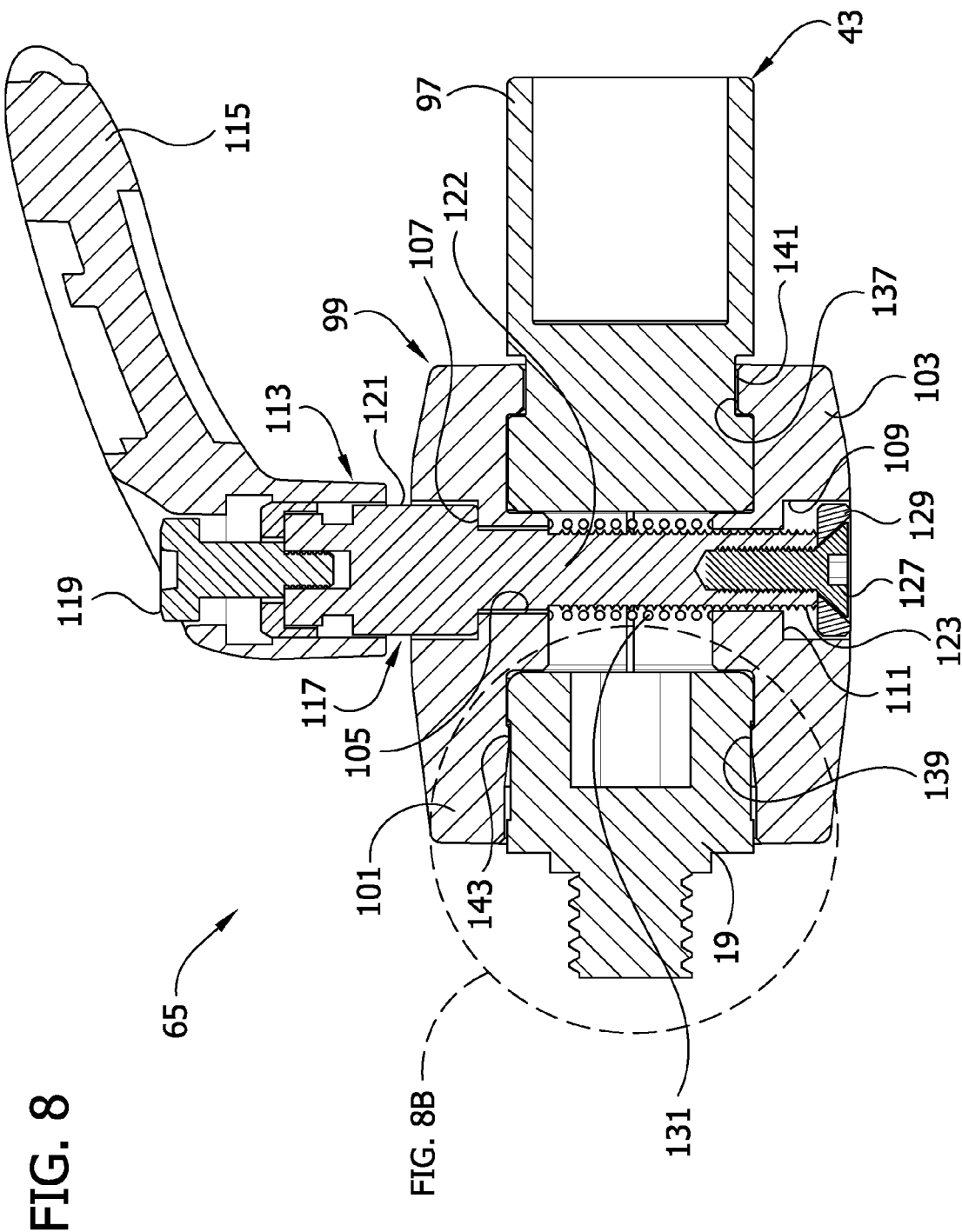
FIG. 8 is a section of the device clamp taken in the plane including line 8-8 of FIG. 7.

Referring now to FIGS. 7 and 8, the device clamp 65 is an intermediate connector for rotational and releasable connection between the flexible shaft 43 and the stem 19 of the pump 5. The device clamp 65 includes a clamp collar 99 having a first (top) clamp element 101 and a second (bottom) clamp element 103. The first clamp element 101 has an opening 105 therein. The opening 105 is shaped like a counterbore and therefore also includes a first shoulder 107. The second clamp element 103 has a threaded, counterbore opening 109 with a second shoulder 111.

Figure 10:
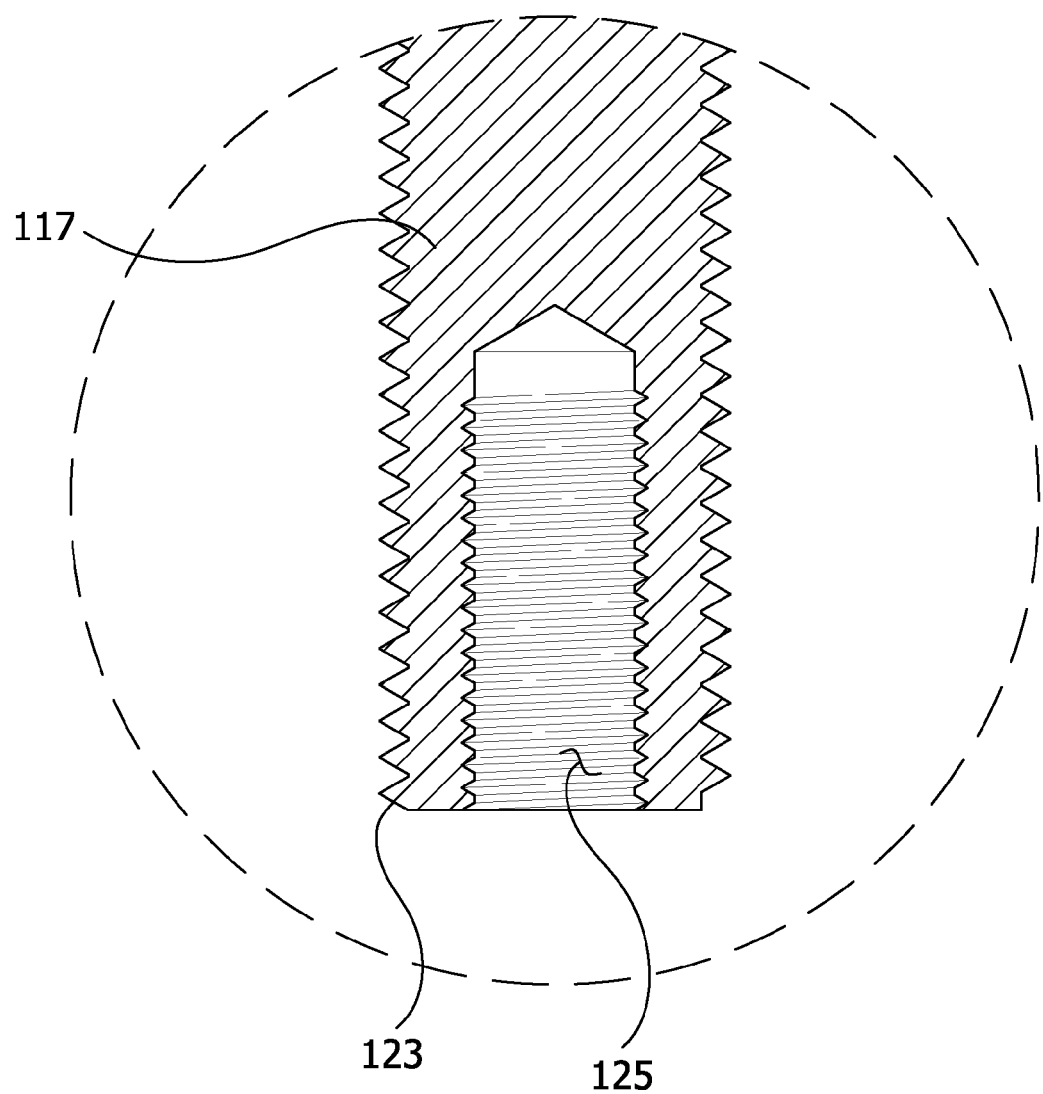
FIG. 10 is an enlarged detail of FIG. 9 in section to reveal internal threads on the screw.

The device clamp 65 also includes an adjustment member, indicated generally at 113. The adjustment member comprises of a lever 115 and a screw 117 (FIG. 8). The lever 115 is rigidly attached to the screw 117 by a threaded fastener 119. The screw comprises a head 121 and a shank 122 including a threaded end portion 123 that has a hole 125 (see, FIG. 10). The screw 117 passes through the opening 105 in the first clamp element 101 and is received in the threaded opening 109 in the second clamp element 103 where the threads on the distal end portion 123 of the shank 122 and the threaded opening in the second clamp element engage. The head 121 of the screw 117 rests on the first shoulder 107 in the first clamp element 101 acting as a brace for the clamping force between the first clamp element and the second clamp element 103 as will be explained in greater detail below.

A threaded fastener 127 passes through the bottom end of opening 109 in the second clamp element and is threadedly received in the hole 125 in the screw 117. The threaded fastener 127 mounts a washer 129 on the free end of the distal end portion 123 of the shank 122. The washer 129 has a sufficiently large diameter to engage the second shoulder 111 of the opening 109 in the second clamp element 103 during operation of the connector 65. A compression spring 131 is positioned around the shank 122 of the screw 117 and its opposite ends bear against the first clamp element 101 and the second clamp element 103, holding the spring in place within the device clamp 65. The compression spring 131 biases the first and second clamp elements 101, 103 away from each other.

Figure 8A:
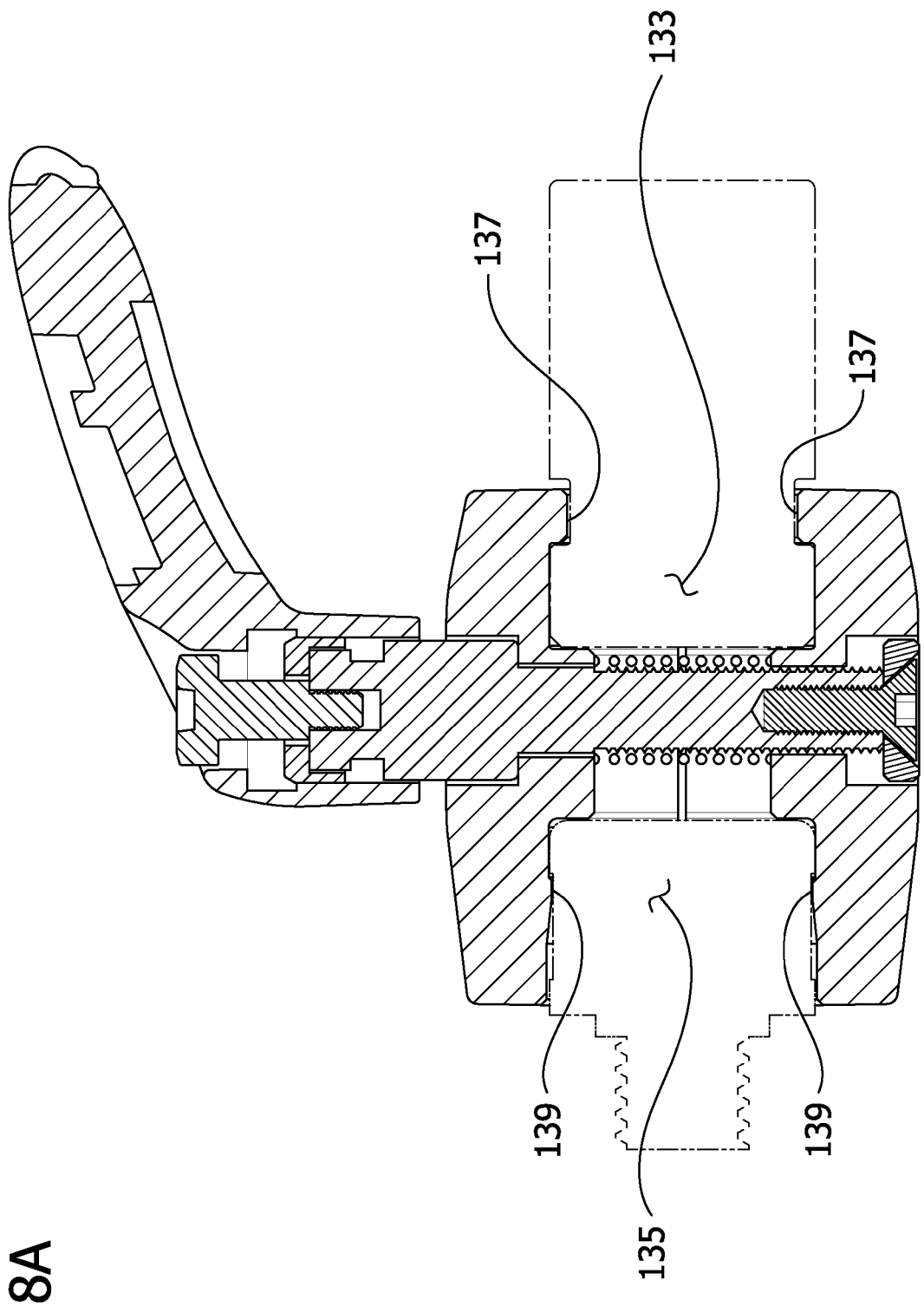
FIG. 8A is the section of the device clamp in FIG. 8 with the stem and sleeve shown in phantom.
Figure 8B:
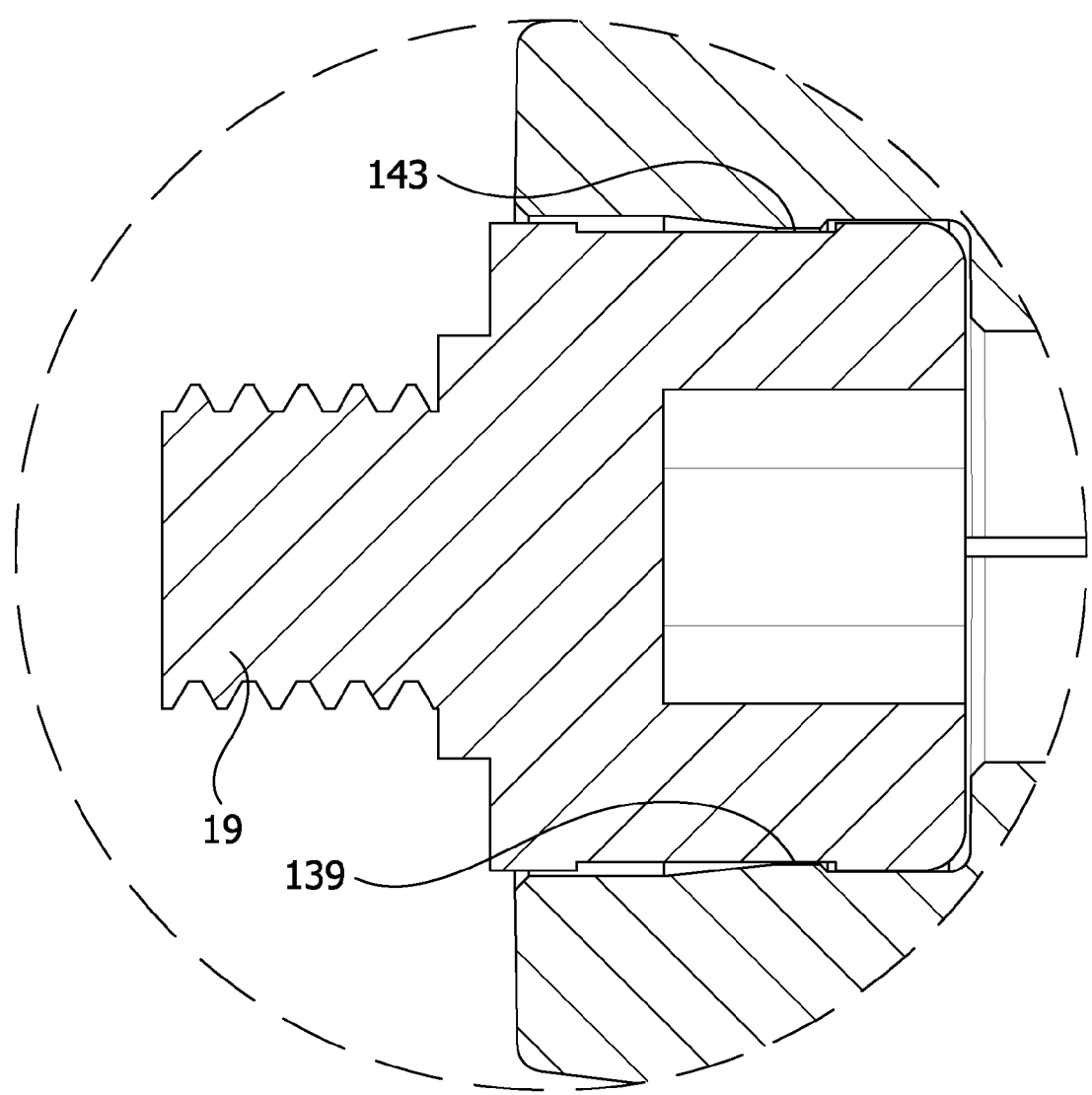
FIG. 8B is an enlarged view of a portion of FIG. 8A showing the connection between the device clamp and the stem.
Figure 9:
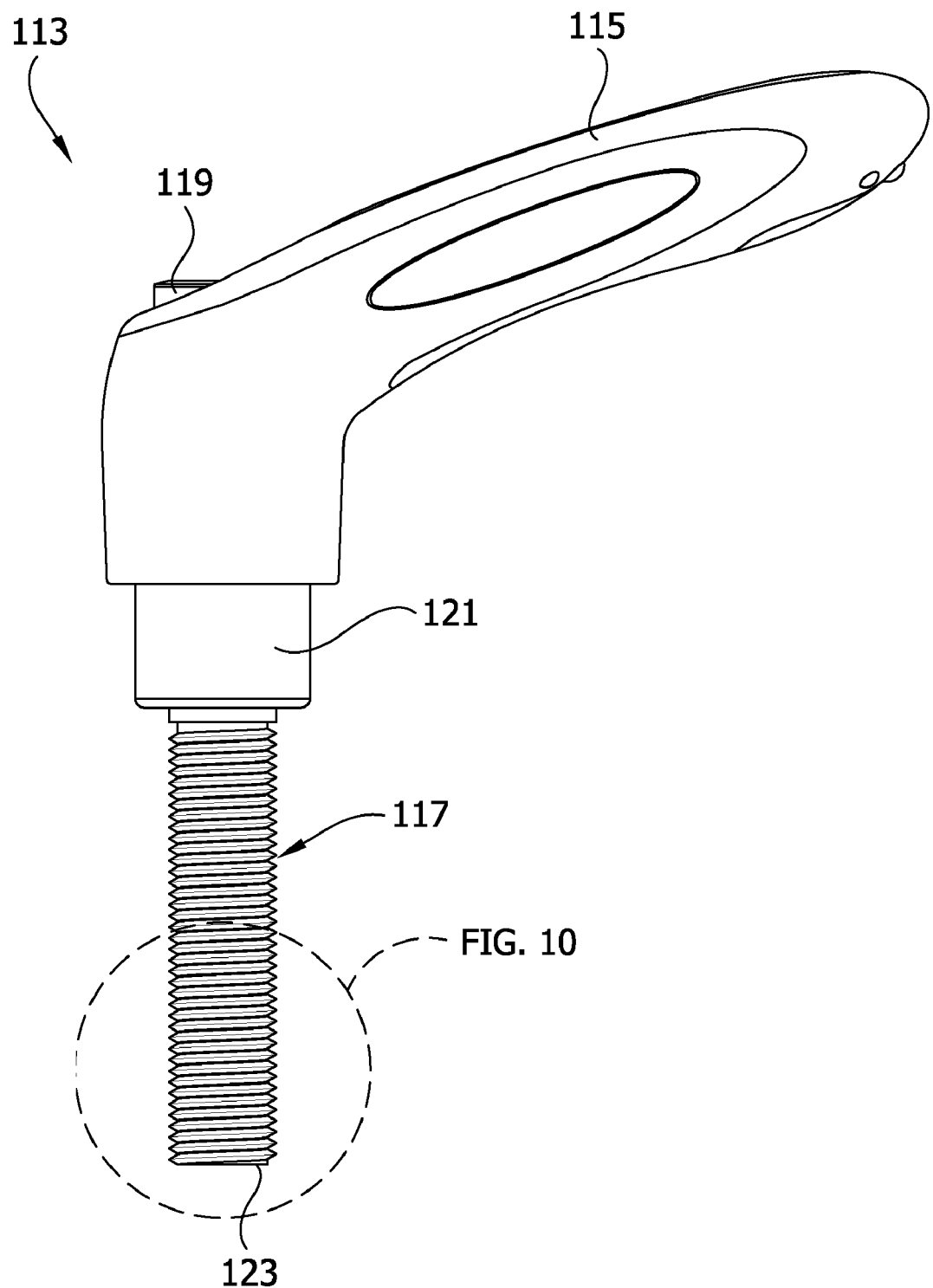
FIG. 9 is a side elevation of a lever and screw attachment of the device clamp.

At each end of the clamp elements 101, 103 the space formed between the two elements define receptacles 133, 135 (see, FIG. 8A). A first receptacle 133 includes a first annular lip 137 (broadly, "a shaft catch") projecting radially inward and extending substantially continuously around the receptacle. A second receptacle 135 includes a second (shallow) annular lip 139 (broadly, "a device catch"), smaller than the first annular lip 137 but also projecting radially inward and extending substantially continuously around the receptacle. The first receptacle 133 is sized and shaped for receiving the sleeve 97 on the second end 47 of the flexible shaft 43, and the second receptacle 135 is sized and shaped for receiving the stem 19 in the pump 5. The sleeve 97 of the flexible shaft 43 includes the first annular recess 141. When the sleeve 97 is received in the first receptacle 133, the annular lip 137 extends into the annular recess 141 allowing the first receptacle to resist withdrawal of the flexible shaft 43. Similarly, the stem 19 in the pump 5 has a second annular recess 143. When the stem 19 is received in the second receptacle 135, the second annular lip 139 extends into the second annular recess 143 providing a mechanical interlock and allowing the second receptacle to resist withdrawal of the pump 5 (see, FIG. 8B).

The device clamp 65 operates in three positions. In a first position, the threaded connection between the screw 117 and the second clamp element 103 is at its tightest. In this position, the first and second clamp elements 101, 103 are closer together so that the elements bear against the sleeve 97 of the flexible shaft 43 and the stem 19 of the pump 5. The two clamp elements 101, 103 fictionally engage the flexible shaft 43 and stem 19, thus prohibiting relative rotation between the flexible shaft 43, clamp collar 99 and the pump 5.

In a second position, the lever 115 is turned a sufficient degree to loosen the thread connection between the screw 117 and the second clamp element 103 so that the first and second clamp elements move apart from one another aided by the bias of the spring 131. This second position will result in a reduction in the frictional force between the clamp collar 99 and the stem 19 permitting the pump 5 to be rotated, within the second receptacle 135, with respect to the flexible shaft 43. The first annular lip 137 in the first receptacle 133 will still extend into the first annular recess 141 on the sleeve 97 thus maintaining connection to the flexible shaft 43. The second annular lip 139 also retains connection of the pump 5 to the flexible shaft 43 in this position. This allows the pump 5 to be rotated to a desired orientation and then secured in that position by turning the lever 115 in the opposite direction. This will tighten the threaded connection between the screw 117 and the second clamp element 103, thus, restoring the frictional engagement between the collar 99 and the stem 19. Those skilled in the art will see that as the first and second elements move apart the frictional force will also be reduced between the clamp collar 99 and the sleeve 97 permitting the collar 99 to rotate in relation to both the pump 5 and the flexible shaft 43. This has the advantage that when the clamp 37 must be attached to a support in an attitude that would otherwise place the lever 115 in a less accessible location the clamp 99 can be rotated around the shaft 43 to place the lever 115 in a more convenient position for operation.

In a third position, the lever 115 is further turned a sufficient additional degree from the second position to loosen the thread connection between the screw 117 and the second clamp element 103 such that the first and second clamp elements move further apart from one another aided by the bias of the spring 131. In this position the second annular lip 139 clears the second annular recess 143. This will result in the complete removal of all circumferential interference between the second annular lip 139 and the stem 19 permitting the pump 5 to move freely into and out of the second receptacle 135. This position will allow the user to handle the pump 5 free from connection to the flexible shaft 43 or allow the pump 5 to be changed out for another device. In this third position the first annular lip 131 will still extend into the first annular recess 141 maintaining connection between the flexible shaft 43 and the device clamp 65.

Figure 11:
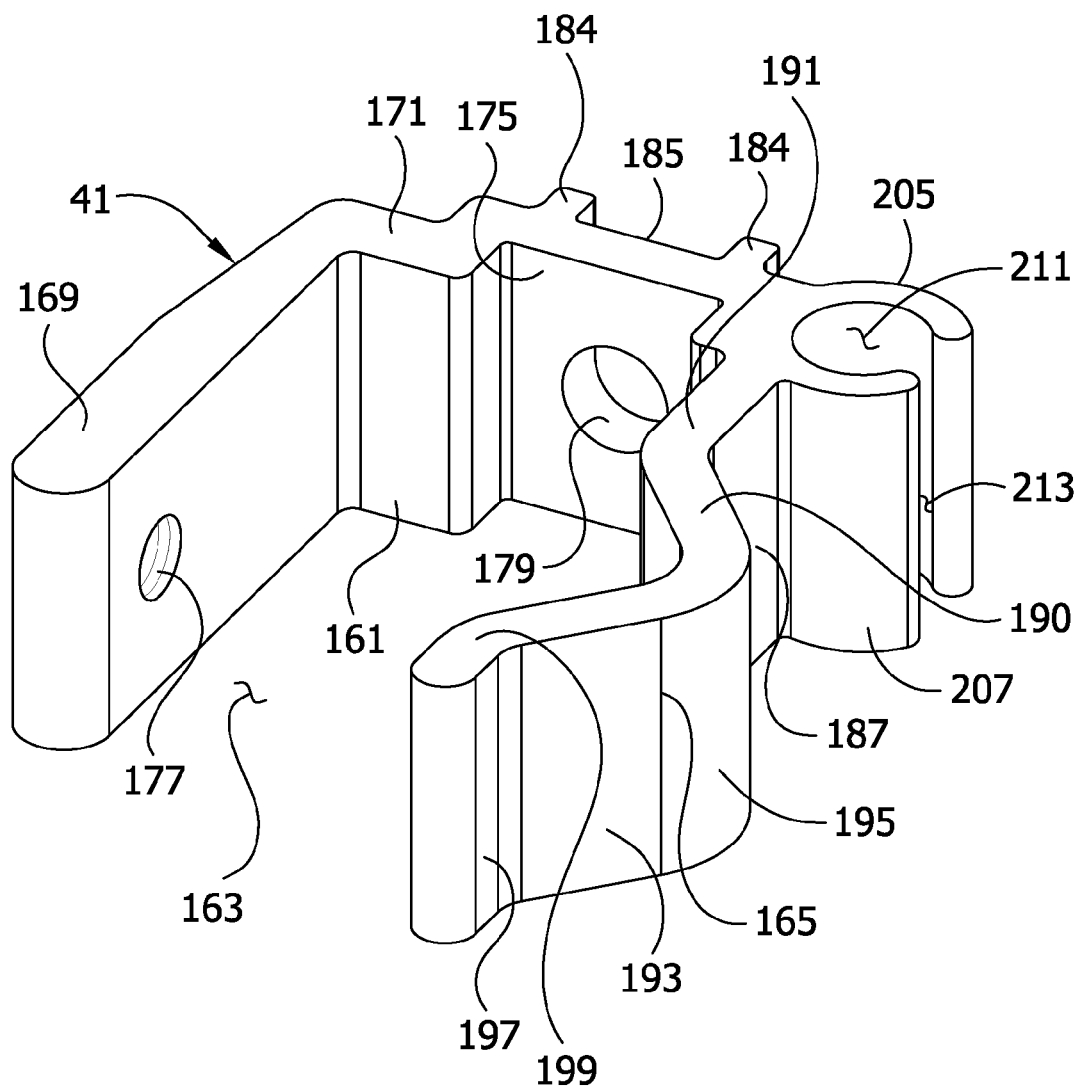
FIG. 11 is an enlarged perspective of a clamping member of the clamping apparatus.
Figure 12:
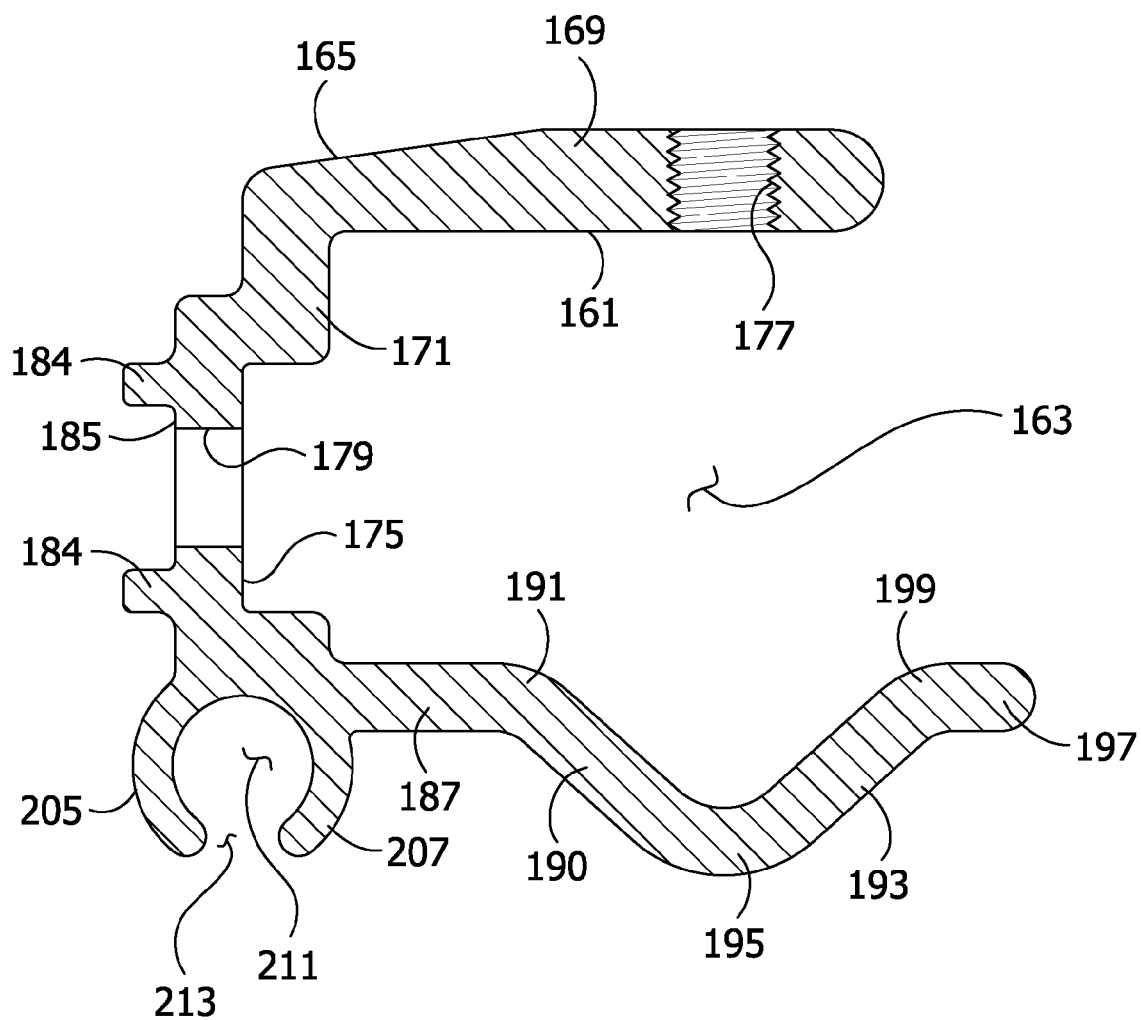
FIG. 12 is a horizontal section of the clamping member of FIG. 11.

As shown in FIGS. 11 and 12, the clamping member 41 is generally C-shaped and has an inner surface, generally indicated 161, for contact with the IV pole or other support member S, an opening 163 for receiving the support member, and an outer surface generally indicated at 165. It is to be understood that clamping members (not shown) having configurations other than described herein may be used within the scope of the present invention. Moreover, the clamping member may be eliminated entirely without departing from the scope of the present invention. Referring to FIG. 12, the clamping member 41 has an upper portion 169 at the top (as oriented in FIG. 12) of the clamping member intersecting a middle portion 171 generally at a right angle. The inner surface 161 on the middle portion 171 has a recess 175. A threaded hole 177 of the clamping member 41 passes through the upper portion 169 and a cylindrical, non-threaded opening 179 passes through the recess 175 in middle portion 171. The middle portion has projecting walls 184 spaced to define a recess 185 that is sized to receive the rectangular protrusion 93 (FIG. 3) on the threaded bushing 63 at the first end 45 of the flexible shaft 43 when the flexible shaft is connected to the clamping member 41.

Figure 13:
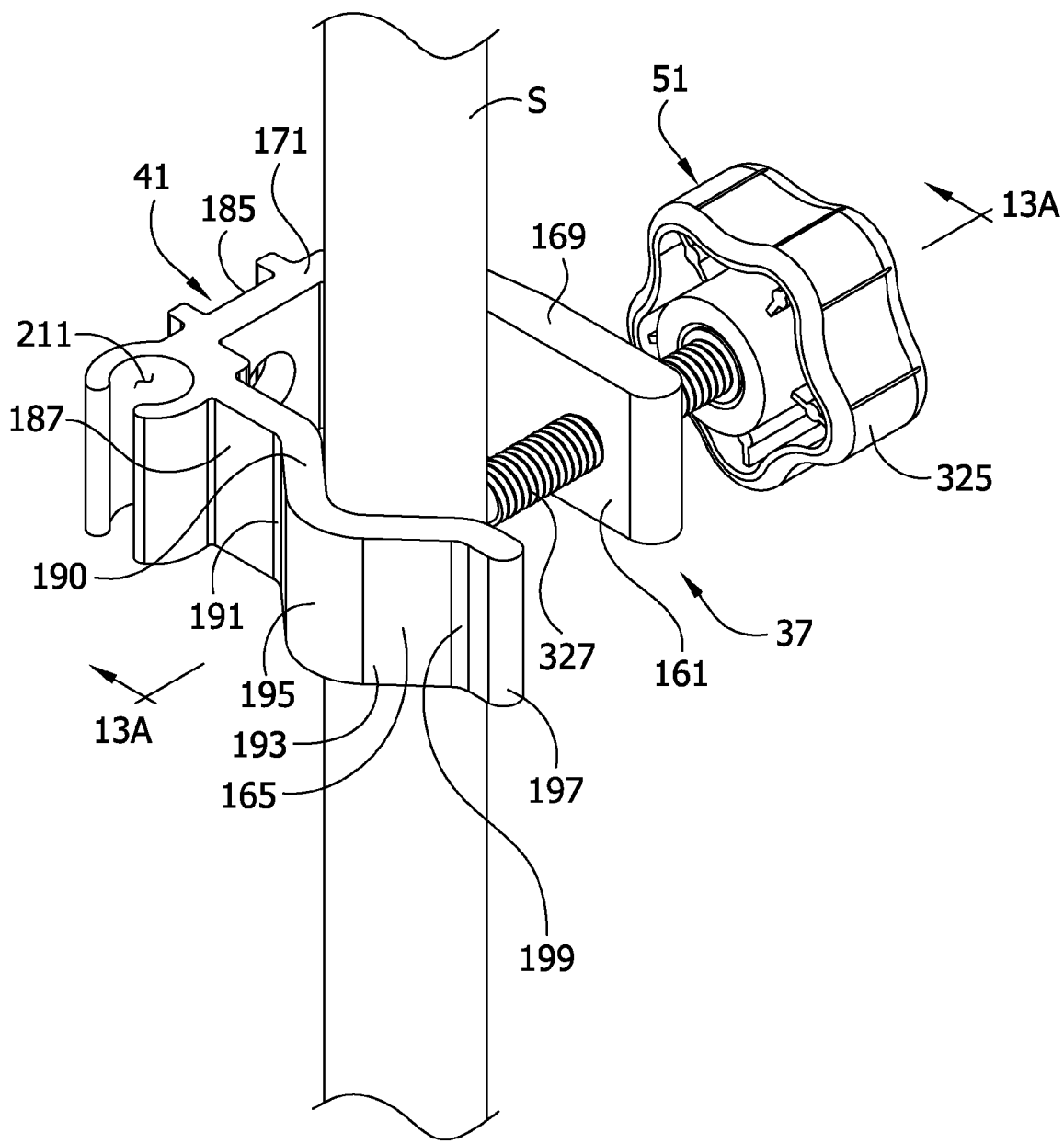
FIG. 13 is a perspective of the clamping member with the flexible shaft removed and a fragmentary portion of a cylindrical pole received in the clamping member.

A first lower portion 187 of the clamping member 41 intersects the middle portion 171 generally at right angles. A second lower portion 190 is downwardly bent relative to the first lower portion 187 so that the first lower portion and the second lower portion meet at a bend 191 having an angle less than 90 degrees. A third lower portion 193 is upwardly bent relative to the second lower portion 190 so that the second and third lower portions meet at a lower bend 195 in the clamping member 41. The second and third lower portions 190, 193 define a "V" to receive an IV pole or support member S (see, FIG. 13). A fourth lower portion 197 is downwardly bent relative to the third lower portion 193 so that the third and fourth lower portions meet at a bend 199. A portion of the inner surface 161 on the fourth lower portion 197 that faces the upper portion 169 is disposed substantially along the same plane as a corresponding surface portion of the first lower portion 187.

As shown in FIGS. 11 and 12, the first lower portion 187 has two roughly semi-cylindrical arms 205, 207 on its outer surface that form a cylindrical recess 211 in the first lower portion. The cylindrical recess 211 provides structure for holding for an AC power adapter cord (not shown) when the cord is not in use. The two arms 205, 207 are separated by an axial slot 213 that allows the power adapter cord or other cord of the pump 5 to be received in the recess 211.

As shown in FIG. 3, the flexible shaft 43 is attached to the clamping member 41 by a threaded bolt 261 or other fastener that is received through the opening 179 in the recess 175 on the middle portion 171 of the clamping member and is in threaded engagement with the internally threaded bushing 63 on the first end 45 of the flexible shaft. The recess 175 is configured to receive the head of the bolt 261 so that the head does not interfere with the support member S when the clamping member 41 is connected to the flexible shaft 43. When the axially outer surface of the threaded bushing 63 on the flexible shaft 43 abuts the outer surface 165 of the middle portion 171 of the clamping member 41, the recess 185 on the middle portion of the clamping member receives the protrusion 93 on the threaded bushing. The engagement of the protrusion 93 on the threaded bushing 63 with the walls 184 prevents the bushing from rotating when the threaded fastener 261 is threadably advanced into the bushing. The threaded connection between the flexible shaft 43 and the clamping member 41 allows the flexible shaft and the clamping member to be disassembled and interchanged with other parts (e.g., a flexible shaft having a longer or shorter length, a flexible shaft having an increased or decreased stiffness, or a clamping member having a different shape) by removing the threaded fastener 261. It is understood that the flexible shaft 43 may be connected to the clamping member 41 with other attachment mechanisms (e.g., quick-disconnect connector, rivet, etc.) without departing from the scope of this invention.

Figure 14:
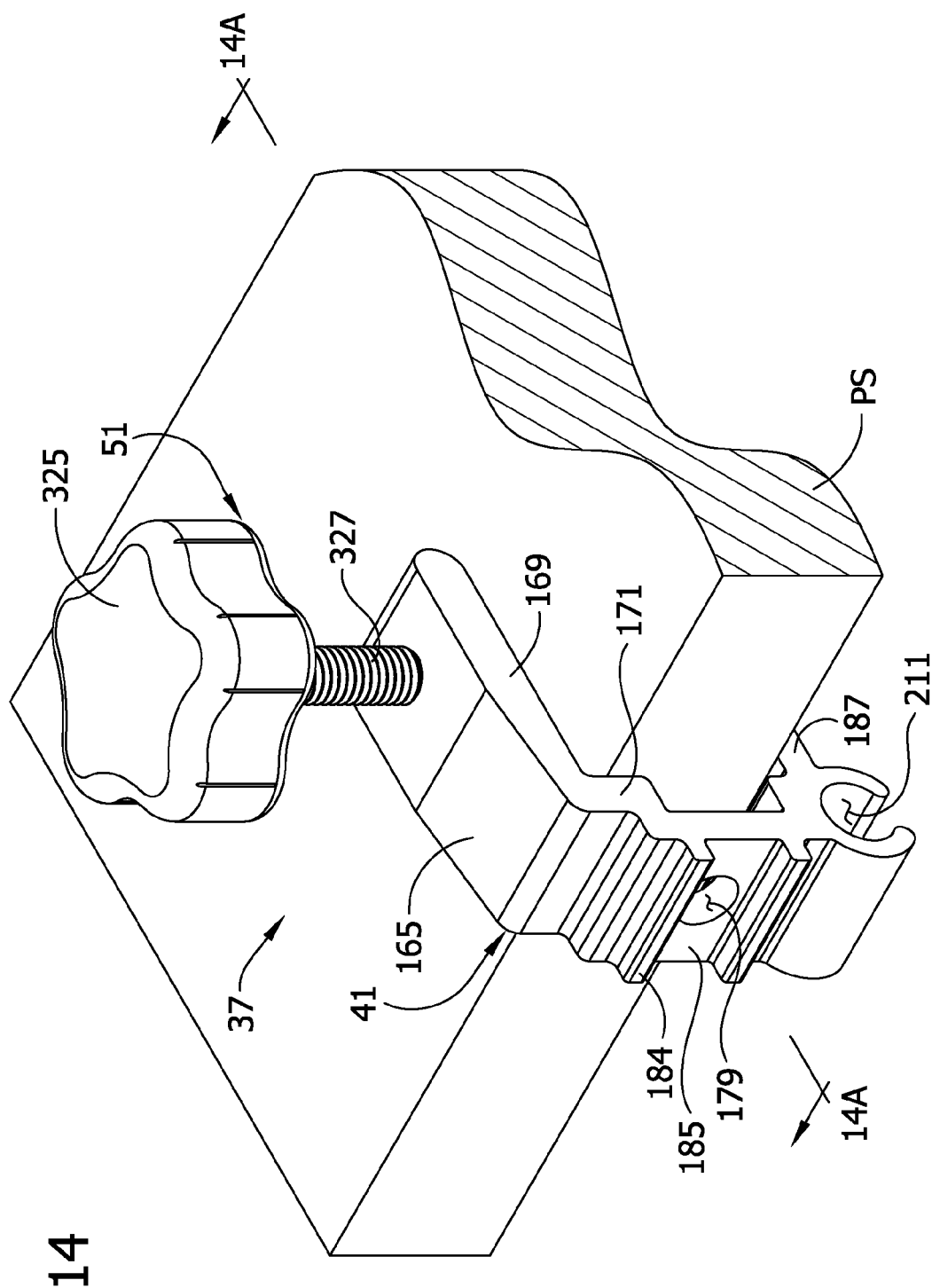
FIG. 14 is a perspective similar to FIG. 13 but with a fragmentary portion of a planar table top received in the clamping member.
Figure 14A:
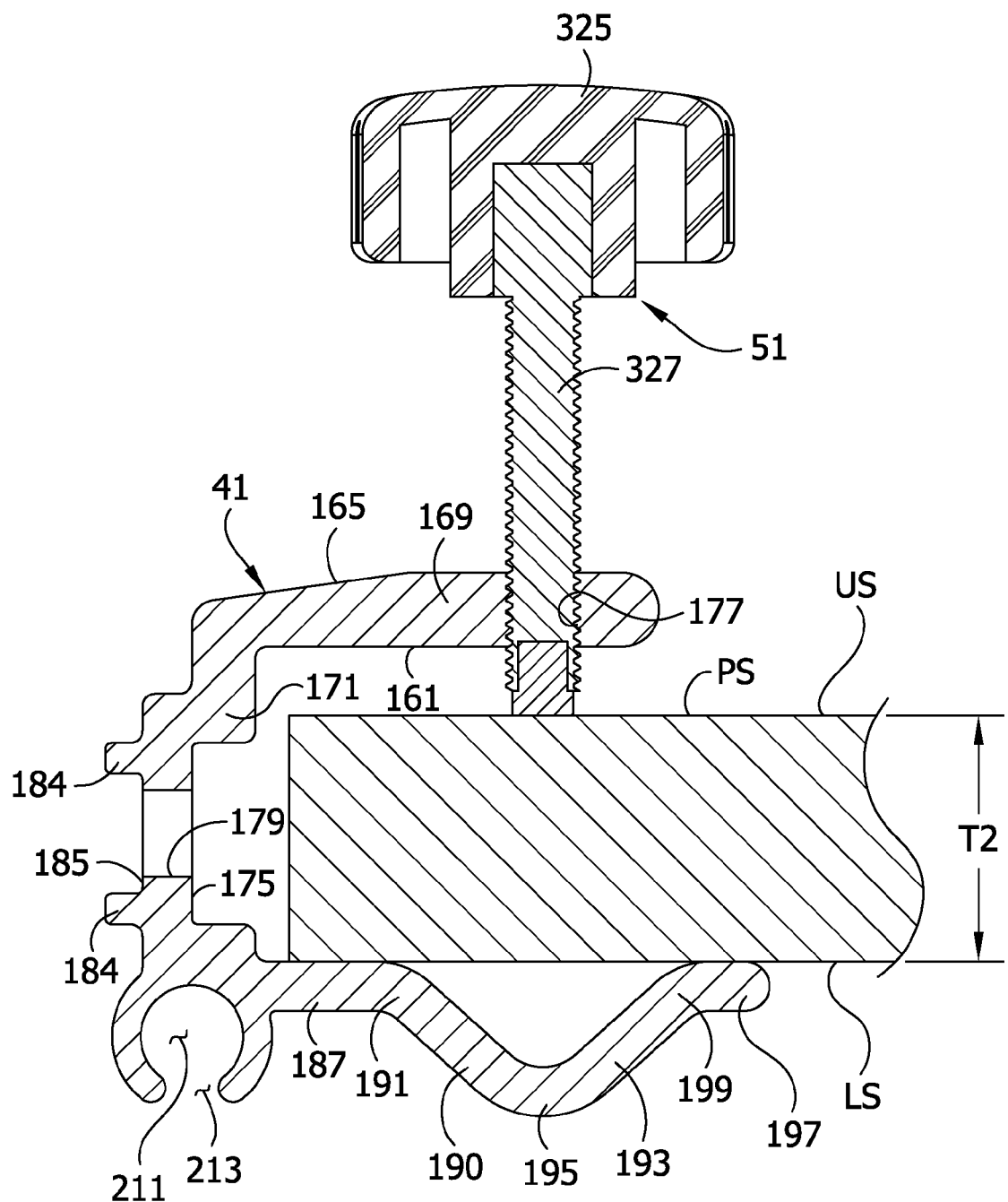
FIG. 14A is a cross-section taken along the plane including 14A-14A of FIG. 14.

It is understood that the clamping member 41 of the present invention allows the pump 5 to be mounted on either a cylindrical surface S (FIGS. 13 and 13A) or a planar surface PS (FIGS. 14 and 14A). Thus the pump 5 may be conveniently mounted in a healthcare environment on an IV pole, horizontal or vertical bed rail, wheelchair tubing, or other support typical of a hospital or other medical facility. In addition, the pump 5 may be mounted on a table top PS or other structure for use in a home or other setting outside of a medical facility. Other suitable support structures for mounting the pump 5 include, but are not limited to, powered medical scooters or mobility chairs, multi-parameter carts, doors, tables, cabinets, bed stands, countertops, chairs, medical trays, television trays, and desks. Further, the clamping member 41 may receive a pole S having a first thickness T1 (FIG. 13A) or a table top PS having a generally planar surface with a thickness T2 (FIG. 14A) that may be greater than or less than the thickness of the pole.

As shown in FIGS. 14 and 14A, the clamping apparatus 3 may be configured for clamping the medical device 5 to a table top or other planar support member PS. In this arrangement, the securing rod 51 is threadably received through the threaded hole 177 of the clamping member 41 to contact the upper surface US of the table top PS. The lower surface LS of the table top PS contacts the inner surface 161 of the first lower portion 187 and fourth lower portion 197 of the clamping member 41 so that the table PS is held in clamped engagement between the securing rod 51 and the clamping member. The clamping apparatus 3 is secured to the table PS by turning the knob 325 on the securing rod 51 so that the rod engages the upper surface US of the table and urges the lower surface LS of the table into secure contact with first and fourth lower portions 187, 197. The substantially co-planar relationship of the first and fourth portions 187, 197 provides stability and orients the middle portion 171 generally perpendicular to the upper and lower surfaces US, LS of the table top PS.

The flexible shaft 43 of the present invention allows six degrees of freedom of motion of the pump 5 relative to the support member S. The pump 5 may be mounted in a first position (FIGS. 1 and 2) in which the pump is retained by the flexible shaft 43 in a stationary position so that a point on the housing 11 (e.g., the front of the housing) is a first distance D1 away from the support. By applying a force to the housing 11 of the pump 5, the flexible shaft 43 may be manipulated so that the pump is moved to a second position (shown in phantom in FIG. 2) in which the pump is retained by the flexible shaft in a stationary position so that the point on the housing is a second distance D2 greater than the first distance D1 from the support member S. It is understood that the pump 5 may be positioned closer to the pole S at the second position such that the distance D2 is less than the first distance D1. Also, the pump 5 may be tilted up or down about a horizontal axis (e.g., x-axis FIGS. 1 and 2) perpendicular to the support S and passing through the pump to allow better viewing of the display screen 13 on the pump. Further, the pump 5 may be tilted left or right about a vertical axis (e.g., y-axis FIGS. 1 and 2) to allow the display screen 13 to be viewed or the controls 15 to be accessed. The pump 5 may be rotated using the device clamp 65 about the horizontal axis A2. The device clamp 65 helps to prevent the spring 69 of the flexible shaft 43 from being unwound by rotation, which can cause a loss of functionality of the flexible shaft. The flexible shaft 43 also allows the pump 5 to be moved anywhere along a line intersecting the support S and the pump so that the only factor limiting the position of the pump relative to the support is the length of the flexible shaft.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above construction without departing from the scope of the invention, it is intended that all matter contained in the above description and shown in the accompanying drawings shall be interpreted as illustrative and not in a limiting sense.

What is claimed is:

1. A clamping apparatus for use in a medical environment to releasably secure a device to a support member, the clamping apparatus comprising:

a flexible shaft having a first end for attachment to the support member and a second end for attachment to the device;

a device clamp adapted to connect the device to the flexible shaft, the device clamp comprising first and second generally opposed clamp elements and a connector interconnecting the first and second clamp elements, the first and second clamp elements defining a first receptacle for receiving the second end of the flexible shaft therein and a second receptacle for receiving a mounting structure of the device therein, at least one of the first and second clamp elements defining a device catch in the second receptacle, the connector being selectively movable between a first position in which the clamp elements are adapted to frictionally engage the second end of the flexible shaft and the mounting structure of the device to resist relative rotation between the flexible shaft, device clamp and device, and a second position in which the clamp elements are relatively farther apart than in the first position and the device catch is positioned to prevent withdrawal of the mounting structure of the device from the second receptacle thereby permitting the device to be rotated with respect to the flexible shaft without releasing connection to the flexible shaft.

2. A clamping apparatus as set forth in claim 1 wherein the device catch comprises a generally annular lip defined by the first and second clamp elements projecting radially inwardly into the second receptacle.

3. A clamping apparatus as set forth in claim 2 wherein the lip extends substantially continuously about the second receptacle.

4. A clamping apparatus as set forth in claim 1 wherein the clamp comprises a shaft catch defined by at least one of the first and second clamp elements in the first receptacle, the shaft catch being positioned to resist withdrawal of the flexible shaft.

5. A clamping apparatus as set forth in claim 4 wherein the device catch projects into the second receptacle a distance less than the shaft catch projects into the first receptacle.

6. A clamping apparatus as set forth in claim 1 wherein the device catch comprises an annular lip projecting into the first receptacle, and wherein the second end of the flexible shaft has a recess therein for receiving the annular lip when the second end of the flexible shaft is received in the first receptacle.

7. A clamping apparatus as set forth in claim 6 wherein the recess extends circumferentially around a longitudinal axis of the flexible shaft.

8. A clamping apparatus as set forth in claim 7 wherein the recess is located inwardly from a termination of the second end of the flexible shaft thereby defining a head receivable in the first receptacle of the device clamp and generally axially opposed to the annular lip in the first and second positions of the connector to capture the second end of the flexible shaft in the first receptacle.

9. A clamping apparatus as set forth in claim 1 wherein the connector is further selectively movable to a third position in which the mounting structure of the device is freely movable into and out of the second receptacle and the second end of the flexible shaft remains captured by the shaft catch in the first receptacle.

10. A clamping apparatus as set forth in claim 1 wherein the connector comprises a screw including a head and a shank, the first clamp element having a bore and the second clamp element having a threaded bore, the shank extending through the bore in the first clamp element and being threadably received in the threaded bore of the second clamp element so that upon rotation of the screw the first and second clamp elements are moved between the first and second positions.

11. A clamping apparatus as set forth in claim 10 wherein the shank is sized and shaped to prevent withdrawal of the shank from the second clamp element thereby retaining the interconnection of the first and second clamp elements.

12. A clamping apparatus as set forth in claim 11 wherein the shank further comprises a washer mounted on a free end of the shank, the washer having a diameter greater than a diameter of the bore in the second clamp element.

13. A clamping apparatus as set forth in claim 10 wherein the head includes a lever projecting generally radially outwardly from the shank for rotating the screw.

14. A clamping apparatus as set forth in claim 13 further comprising a compression spring arranged for biasing the first and second clamp elements away from each other.

15. A clamping apparatus as set forth in claim 1 further comprising a clamping member for connecting the flexible shaft to the support member, the clamping member having a portions lying generally in a coplanar relation and separated by a portion defining a non-coplanar, recessed section adapted to receive cylindrical structure therein.

16. A clamp for use in connecting a medical device to a support, the clamp comprising:
   first and second generally opposed clamp elements; and
   a connector interconnecting the first and second clamp elements;
   the first and second clamp elements defining a first receptacle for receiving an end of the support therein and a second receptacle for receiving a mounting structure of the medical device therein, at least one of the first and second clamp elements defining a device catch in the second receptacle, the connector being selectively movable between a first position in which the clamp elements are adapted to frictionally engage the end of the support and the mounting structure of the device to resist relative rotation between the support, clamp and medical device, and a second position in which the clamp elements are relatively farther apart than in the first position and the device catch is positioned to prevent withdrawal of mounting structure of the medical device from the second receptacle thereby permitting the device to be rotated with respect to the support without releasing connection to the support.

17. A clamp as set forth in claim 16 wherein the device catch comprises a generally annular lip defined by the first and second clamp elements projecting radially inwardly into the second receptacle.

18. A clamp as set forth in claim 17 wherein the lip extends substantially continuously about the second receptacle.

19. A clamp as set forth in claim 16 further comprising a support catch defined by at least one of the first and second clamp elements in the first receptacle, the device catch being positioned to resist withdrawal of the support in the second position of the clamp elements.

20. A clamping apparatus as set forth in claim 19 wherein the device catch projects into the second receptacle a distance less than the support catch projects into the first receptacle.

21. A clamp as set forth in claim 16 wherein the connector is further selectively movable to a third position in which the mounting structure of the medical device is freely movable into and out of the second receptacle and the end of the support remains captured by the support catch in the first receptacle.

22. A clamp as set forth in claim 16 wherein the connector comprises a screw including a head and a shank, the first clamp element having a bore and the second clamp element having a threaded bore, the shank extending through the bore in the first clamp element and being threadably received in the threaded bore of the second clamp element so that upon rotation of the screw the first and second clamp elements are moved between the first and second positions.

23. A clamp as set forth in claim 20 wherein the shank is sized and shaped to prevent withdrawal of the shank from the second clamp element thereby retaining the interconnection of the first and second clamp elements.

24. A clamp as set forth in claim 23 wherein the shank further comprises a washer mounted on a free end of the shank, the washer having a diameter greater than a diameter of the bore in the second clamp element.

25. A method of supporting a medical device on a flexible shaft to permit selective rotation of the medical device relative to the flexible shaft without loss of interconnection with the flexible shaft, the method comprising:

rotating a connector to move first and second clamp elements to an open position;

inserting a mounting structure of the medical device into a receptacle defined by the first and second clamp elements;

rotating the connector to move the first and second clamp elements to a fully closed position thereby clamping the flexible shaft and mounting structure for resisting relative rotation of the mounting structure relative to the flexible shaft;

loosening the clamp to a position in which the mounting structure and medical device are free to rotate, while the medical device is retained from moving out of the receptacle.

* * * * *